United States Patent
Moffat et al.

(10) Patent No.: US 8,778,953 B2
(45) Date of Patent: Jul. 15, 2014

(54) INHIBITORS OF P38 MAP KINASE

(75) Inventors: David Festus Charles Moffat, Abingdon (GB); Stephen John Davies, Abingdon (GB); Stephane Pintat, Abingdon (GB)

(73) Assignee: Chroma Therapeutics Ltd., Abingdon (GB)

( * ) Notice: Subject to any disclaimer, the term of this patent is extended or adjusted under 35 U.S.C. 154(b) by 431 days.

(21) Appl. No.: 12/867,774

(22) PCT Filed: Feb. 27, 2009

(86) PCT No.: PCT/GB2009/000553
§ 371 (c)(1),
(2), (4) Date: Aug. 16, 2010

(87) PCT Pub. No.: WO2009/106844
PCT Pub. Date: Sep. 3, 2009

(65) Prior Publication Data
US 2011/0034520 A1 Feb. 10, 2011

(30) Foreign Application Priority Data

Feb. 29, 2008 (GB) .................................. 0803748.3
Aug. 27, 2008 (GB) .................................. 0815544.2

(51) Int. Cl.
*A01N 43/54* (2006.01)
*A61K 31/505* (2006.01)
*A01N 43/40* (2006.01)
*A61K 31/44* (2006.01)
*C07D 239/02* (2006.01)
*C07D 213/72* (2006.01)

(52) U.S. Cl.
USPC ............ 514/269; 514/345; 544/298; 546/297

(58) Field of Classification Search
USPC ..................... 514/269, 345; 544/298; 546/297
See application file for complete search history.

(56) References Cited

U.S. PATENT DOCUMENTS

| 5,331,006 | A  | 7/1994  | Horwell et al. |
| 6,448,256 | B1 | 9/2002  | Wright et al. |
| 2005/0256102 | A1 | 11/2005 | Claiborne et al. |
| 2006/0046999 | A1 | 3/2006  | Alonso-Alija et al. |

FOREIGN PATENT DOCUMENTS

| EP | 0505321 A2 | 9/1992 |
| WO | 03076405 A | 9/2003 |
| WO | 2004/113336 A1 | 12/2004 |
| WO | 2005/046575 A2 | 5/2005 |
| WO | 2005/072061 A2 | 8/2005 |
| WO | 2006117567 A | 11/2006 |
| WO | 2007129040 A | 11/2007 |
| WO | 2008/053158 A1 | 5/2008 |
| WO | 2009/060160 A1 | 5/2009 |

OTHER PUBLICATIONS

International Search Report for PCT/GB2009/000553 dated May 8, 2009.
Shricker, Bettina, Klaus Thirring, and Heinz Berner Chymotrypsin Catalyzed Enantioselective Hydrolysis of Alkenyl-a-Amino Acid Esters, Bioorganic & Medicinal Chemistry Letters, vol. 2, No. 5, pp. 387-390, (1992).
Yee, Christopher, Todd A. Blythe, Thomas J. McNabb, and Alan E. Walts. Biocatalytic Resolution of Tertiary a-Substituted Carboxylic Acid Esters: Efficient Preparation of a Quaternary Asymmetric Carbon Center. J. Org. Chem. 1992, 57, pp. 3525-3527.
Han et al, A MAP Kinase Targeted by Endotoxin and Hyperomolarity in Mammalian Cells Science 1994, vol. 265, pp. 808-811, 4 pages.
Salituro et al, Inibitors of p38 MAP Kinase: Therapeutic Cytokine-Mediated Diseases, Current Medicinal Chemistry, 1999, vol. 6, pp. 807-823, 17 pages.
Yong Jiang et al, "Characterization of the Structure and Function of a New Mitogen-activated Protein Kinase (p38β)*" The Journal of Biological Chemistry, vol. 271, No. 30, Issue of Jul. 26, pp. 17926, 1996.
Zhuangjie Li et al.; "The Primary Structure of p38g: A New Memeber of p38 Group of MAP Kinases," Biochemical and Biophysical Researc h Communications 228, 334-340, (1996).
Young Jiang et al., "Characterization of the Structure and Function of the Fourth Member of p38 Group Mitogen-activated Protein Kinases, p38d*," The Journal of Biological Chemistry, vol. 272, No. 48, Issue of Nov. 28, pp. 30122-30128, 1997.
Ana Cuenda et al., "SB 203580 is a specific inhibitor of a MAP kinase homologue which is stimulated by cellular stresses and interleukin-1," FEBS Letters 364 (1995) 229-233.
Alexey Kotlyarov et al., "MAPKAP kinase 2 is essential for LPS-induced TNF-a biosynthesis," Nature Cell Biology, vol. 1, Jun. 1999, 94-97.

(Continued)

*Primary Examiner* — Sarah Pihonak
(74) *Attorney, Agent, or Firm* — Fulbright & Jaworski LLP

(57) ABSTRACT

Compounds of formula (I) are p38 MAP kinase inhibitors useful for the treatment of autoimmune and inflammatory diseases: wherein: G is —N= or —CH=; D is an optionally substituted divalent mono- or bi-cyclic aryl or heteroaryl radical having 5-13 ring members; R6 is hydrogen or optionally substituted $C_rC_3$ alkyl; P represents hydrogen and U represents a radical of formula (IA); or U represents hydrogen and P represents a radical of formula (IA); wherein A represents an optionally substituted divalent mono- or bicyclic carbocyclic or heterocyclic radical having 5-13 ring members; z is O or 1; —$X^1$-$L^1$-Y— is a linker radical or bond; $R_1$ is a carboxylic acid group (—COOH), or an ester group which is hydrolysable by one or more intracellular esterase enzymes to a carboxylic acid group; and $R_2$ and $R_3$ are as defined in the claims.

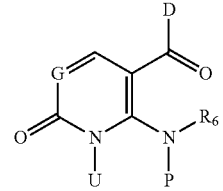

—A—$(CH_2)_z$—$X^1$—$L^1$—Y—NH—$CR_1R_2R_3$ (IA)

17 Claims, No Drawings

(56) References Cited

OTHER PUBLICATIONS

Katrin Engel et al., "Leptomycin B-sensitive nuclear export of MAPKAP kinase 2 is regulated by phosphorylation," The EMBO Journal, vol. 17, No. 12, pp. 3363-3371, 1998.

Wuyi Meng et al., "Structure of Mitogen-activated Protein Kinase-activated Protein (MAPKAP) Kinase 2 Suggests a Bifunctional Switch That Couples Kinase Activation with Nuclear Export*," The Journal of Biological Chemistry, vol. 277, No. 40, Issue of Oct. 4, pp. 37401-37405, 2002.

Marlyn L. Foster et al., "Potential of p38 Inhibitors in the Treatment of Rheumatoid Arthritis," Drug News Perspect 13, Oct. 2000, 488-497.

Sanjay Kumar et al., "P38 MAP Kinases: Key Signalling Molecules As Therapeutic Tar-Gets for Inflammatory Diseases," Nature Reviews Drug Discovery, vol. 2, Sep. 2003, 717-726.

Laszlo Revesa et al., "SAR of 4-Hydroxypiperidine and Hydroxyalkyl Substituted Heterocycles as Novel p38 Map Kinase Inhibitors," Bioorganic & Medicinal Chemistry Letters 10, (2000), 1261-1264.

Scott A. Wadsworth et al., "RWJ 67657, a Potent, Orally Active Inhibitor of p38 Mitogen-Activated Protein Kinase," The Journal of Pharamacology and Experimental Therapeutics, vol. 291, No. 2, Accepted for publication Jul. 22, 1999, 680-687.

Woody Denham et al., "Inhibition of p38 mitogen activate kinase attenuates the severity of pancreatitis-induced adult respiratory distress syndrome," Crit Care Med 2000, vol. 28, No. 7, 2567-2572.

Jun Yang et al., "Evidence of a central role for p38 map kinase induction of tumor necrosis factor a in pancreatitis-associated pulmonary injury," Surgery 1999: 126: 216-22.

David C. Underwood et al., "SB 239063, a Potent p38 MAP Kinase Inhibitor, Reduces Inflammatory Cytokine Production, Airways Eosinophil Infiltration, and Persistence," The Journal of Pharmacology and Experimental Therapeutics, vol. 293, No. 1, 293: 281-288, 2000.

Georg H. Waetzig et al., "p38 Mitogen-Activated Protein Kinase Is Activated and Linked to TNF-a Signaling in Inflammatory Bowel Disease," The Journal of Immunology, 2002, 168, 5432-5351.

Thomas M. Behr et al., "Hypertensive End-Organ Damage and Premature Mortality Are p38 Mitogen-Activated Protein Kinase-Dependent in a Rat Model of Cardiac Hypertropy and Dysfunction" Circualation. 2001; 104:1292-1298.

F.C. Narone et al., "SB 239063, a Second-Generation p38 Mitogen-Activated Protein Kinase Inhibitor, Reduces Brain Injury and Neurological Deficits in Cerebral Focus lschemia," The Journal of Pharamacology and Experimental Therapeutics, vol. 296, No. 2, 296:312-321, 2001.

Joel A. G. van Roon et al., "Selective Elimnation of Synovial Inflammatory Macrophages in Rheumatoid Arthritis by an Fcg Receptor I-Directed Immunotoxin," Arthritis & Rheumatism, vol. 48, No. 5, May 2003, pp. 1229-1238.

Antonella Naldini et al., "Role of Inflammatory Mediators in Angiogenesis," Current Drug Targets—Inflammation & Allergy, 2005, 4, 3-8.

I. Sanchez_perez et al., "FK506 sensitizes mamalian cells to high osmolarity by modulating p38 MAP kinase activation," CMLS Celluar and Molecular Life Sciences, vol. 61, No. 6, 2004, pp. 700-708.

Zhongui Guan et al., "p38 MAP Kinase Mediates Both Short-Term and Long-Term Synaptic Depression in Aplysia," The Official Journal of the Society for Neuroscience 13, 2003, vol. 23, No. 19 pp. 7317-7325.

Daniel W. Szeto et al., "Human Thymidylate Synthetase—III," Biochemical Pharamacology, vol. 28, pp. 2633-2637, human thymidylate, (1979).

A. Rosowsky et al., "Methotrexate Analogues. 18. Enhancement of the Antitumor Effect of Methotrexate and 3', 5'-Dichloromethotrexate by the Use of Lipid-Soluble Diesters," Journal of Medicinal Chemistry, vol. 26, No. 10, 1983, pp. 1448-1452.

James J. Fort et al., "Physicochemical properties and chromatographic behavior of a homologus series of methotrexate-a, g-dialkyl ester prodrugs," International Journal of Pharmaceutics, vol. 36, No. 1, 1987, pp. 7-16.

Jerry I. McCullough et al., "Effect of Lipid-Soluble Esters of Methotrexate on DNA Synthesis in Human Skin," Journal of Investigative Dermatology, vol. 63, No. 6, 1974, pp. 464-466.

Jerry L. McCullough et al., "In Vitro Screening of Biochemical Activity of Folic Acid Antagonists in Skin," Journal of Investigative Dermatology, vol. 68, No. 1977, pp. 362-365.

Andre Rosowsky et al., "Methotrexate Analogues. 11. Unambiguous Chemical Synthesis and in Vitro Biological Evaluation of a- and g-Monoesters as Potential Prodrugs," Journal of Medicinal Chemistry, vol. 21, No. 4, 1978, pp. 380-386.

Rosowsky et al., Biochemical Pharmacology, vol. 29, np. 4, 1980, pp. 648-652.

Andre Rosowsky et a;., "Methotrexate Analogues. 21. Divergent Influence of Alkyl Chain Length on the Dihydrofolate Reductase Affinity and Cytotoxicity of Methotrexate Monoesters," Journal of Medicinal Chemistry, vol. 27, No. 5, 1984, pp. 605-609.

Yu Li et al., "Methotrexate Esters of Poly(Ethylene Oxide)-Block-Poly(2-Hydroxyethyl-L-Aspartamide). Part I: Effects of the Level of Methotrexate Conjugation on the Stability of Micelles and on Drug Release," Pharmaceutical Research, vol. 17, No. 5, 2000, pp. 607-611.

Timothy J. Thornton et al., "Quinazoline Antifolate Thymidylate Synthase Inhibitors: Difluoro-Substituted Benzene Ring Anaologues," Journal of Medicinal Chemistry, vol. 35, No. 12, 1992, pp. 2321-2327.

Giovanni M. Pauletti et al. "Esterase-Sensitive Cyclic Prodrugs of Peptides: Evaluation of a Phenylpropionic Acid Promoiety in a Model Hexapeptide," Pharmaceutical Research, vol. 14, No. 1, 1997, pp. 11-17.

Terence R. Jones et al., "Synthesis and Biological Properties of 3-Methyl-10-propargyl-5, 8-dideazafolic Acid," Journal of Heterocyclic Chemistry, vol. 26, 1989, pp. 1501-1507.

David Orain et al., "From Solution-Phase Studies to Solid-Phase Synthesis: A New Indole Based Scaffold for Combinatorial Chemistry," vol. 57, No. 5, 2003, pp. 255-261.

Kazuhiko Tamiki et al., "Synthese and Structure-Activity Relationships of Gelatinase Inhibitors Derived from Matlystatins," Chemical and Pharmaceutical Bulletin, vol. 43, No. 11, 1995, pp. 1883-1893.

Hartmut Schirok et al., "Efficient Regioselective Synthesis of 6-Amino-5-benzoyl-1-Substituted 2(1H)-Pyridinones," J. Org. Chem. 2005, vol. 70, 9463-9469.

Norman A. Lebel et al., "The Addition of Nitrones to Olefins. Fused Bicyclic Isoxazolidines," Contribution from the Department of Chemistry, Wayne State University, Detroit 2, Mich, 1964, 86, 3759.

Richard F. Borch., "The Cyanohydridoborate Anion as a Selective Reducing Agent," Contribution from the Department of Chemistry, University of Minnesota, 1971, 93, 2897.

oyo Mitsunobu et al., "Preparation of Esters of Carboxylic and Phosphoric Acid via Quaternary Phosphonium Salts," Bulletin of the Chemical Society of Japan, vol. 40, 1967, 2380-2382.

Anand S. Dutta et al., "Inhibitors of Human Renin. Cylic Peptide Analogues Containing a D-Phe-Lys-D-Trip Sequence," Journal of Medicinal Chemistry, vol. 33, 1990, pp. 2560-2568.

Imai, Teruko, "Human Carboxylesterase Isozymes: Catalytic Properties and Rational Drug Design"; Drug Metab. Pharmacokinet, 2006, vol. 21, No. 3, pp. 173-185.

Charlton et al; "Monocyte and macrophage selective anti-inflammatory kinase inhibitors"; Med Chem. Commun, 2012, vol. 3, pp. 1070-1076.

INHIBITORS OF P38 MAP KINASE

CROSS REFERENCE TO RELATED APPLICATIONS

This application is a National Stage application of co-pending PCT application PCT/GB2009/000553 filed Feb. 27, 2009, which application claims priority from Great Britain Application No. 0803748.3 filed Feb. 29, 2008 and Great Britain Application No. 0815544.2 filed Aug. 27, 2008. The above mentioned applications are incorporated herein by reference in their entirety.

This invention relates to a series of amino acid esters, to compositions containing them, to processes for their preparation and to their use in medicine as p38 MAP kinase inhibitors for the treatment of autoimmune and inflammatory diseases, including rheumatoid arthritis, psoriasis, inflammatory bowel disease, Crohns disease, ulcerative colitis, chronic obstructive pulmonary disease, asthma, multiple sclerosis, diabetes, atopic dermatitis, graft versus host disease, systemic lupus erythematosus and others.

BACKGROUND OF THE INVENTION

Inappropriate activation of leukocytes including monocytes, macrophages and neutrophils leading to the production of elevated levels cytokines such as TNF-α, IL1-β and IL-8, is a feature of the pathogenesis of several inflammatory diseases including rheumatoid arthritis, ulcerative colitis, Crohn's disease, chronic obstructive pulmonary disease (COPD), asthma and psoriasis. The production of cytokines by inflammatory cells is a result of response to a variety of external stimuli, leading to the activation of a number of intracellular signalling mechanisms. Prominent amongst these is the mitogen-activated protein kinase (MAPK) superfamily consisting of highly conserved signalling kinases that regulate cell growth, differentiation and stress responses. Mammalian cells contain at least three families of MAPKs: the p42/44 extracellular signal-regulated kinase (ERK) MAPKs, c-Jun NH2-terminal kinases (JNKs) and p38 MAPK (also termed p38α/Mpk2/RK/SAPK2α/CSBP1/2). p38 MAPK was first cloned following its identification as a kinase that is tyrosine phosphorylated after stimulation of monocytes by lipopolysaccharide (LPS) [Han et al, Science 1994,265,808]. Additional homologues of mammalian p38 have been described and include p38β [Jiang et al, J. Biol. Chem., 1996, 271, 17920], p38γ [Li et al, Biochem. Biophys. Res. Commun. 1996, 228, 334] and p38δ [Jiang et al, J. Biol. Chem. 1997, 272, 30122]. While p38α and p38β are ubiquitously expressed, p38γ is restricted primarily to skeletal muscle and p38δ is predominantly expressed in lung and kidney.

The release of cytokines by host defense cells and the response of leukocytes to cytokines and other pro-inflammatory stresses are to varying extent regulated by p38 MAPK [Cuenda et al, FEBS Lett, 1995, 364, 229-233]. In other cell types, p38 MAPK controls stress responses such as the production of IL-8 by bronchial epithelial cells stimulated by TNF-α, and the up-regulation of the cell adhesion molecule ICAM-1 in LPS-stimulated endothelial cells. Upon activation, via dual phosphorylation of a TGY motif by the dual specificity kinases MKK3 and MKK6, p38 MAPK exerts its effects through phosphorylation of transcription factors and other kinases. MAP kinase-activated protein kinase-2 (MAPKAPK-2) has been identified as a target for p38 phosphorylation. It has been demonstrated that mice [Kotlyarov et al, Nat. Cell Biol. 1999, 1, 94-97] lacking MAPKAPK-2 release reduced levels of TNF-α, IL-1β, IL-6, IL-10 and IFN-γ in response to LPS/galactosamine mediated endotoxic shock. The regulation of the levels of these cytokines as well as COX-2 is at the mRNA level. TNF-α levels are regulated through translational control via AU-rich elements of the 3'-UTR of TNF-α mRNA, with MAPKAPK-2 signalling increasing TNF-αmRNA translation. MAPKAPK-2 signalling leads to increased mRNA stability for COX-2, IL-6 and macrophage inflammatory protein. MAPKAPK-2 determines the cellular location of p38 MAPK as well as transducing p38 MAPK signalling, possessing a nuclear localisation signal at its carboxyl terminus and a nuclear export signal as part of its autoinhibitory domain [Engel et al, EMBO J. 1998, 17, 3363-3371]. In stressed cells, MAPKAPK-2 and p38 MAPK migrate to the cytoplasm from the nucleus, this migration only occurring when p38 MAPK is catalytically active. It is believed that this event is driven by the exposure of the MAPKAPK-2 nuclear export signal, as a result of phosphorylation by p38 MAPK [Meng et al, J. Biol. Chem. 2002, 277, 37401-37405]. Additionally p38 MAPK either directly or indirectly leads to the phosphorylation of several transcription factors believed to mediate inflammation, including ATF1/2 (activating transcription factors 1/2), CHOP-10/GADD-153 (growth arrest and DNA damage inducible gene 153), SAP-1 (serum response factor accessory protein-1) and MEF2C (myocyte enhancer factor-2) [Foster et al, Drug News Perspect. 2000, 13, 488-497].

It has been demonstrated in several instances that the inhibition of p38 MAPK activity by small molecules, is useful for the treatment of several disease states mediated by inappropriate cytokine production including rheumatoid arthritis, COPD, asthma and cerebral ischemia. This modality has been the subject of several reviews [Salituro et al, Current Medicinal Chemistry, 1999, 6, 807-823 and Kumar et al, Nature Reviews Drug Discovery 2003, 2, 717-726].

Inhibitors of p38 MAPK have been shown to be efficacious in animal models of rheumatoid arthritis, such as collagen-induced arthritis in rat [Revesz et al, Biorg. Med. Chem. Lett., 2000, 10, 1261-1364] and adjuvant-induced arthritis in rat [Wadsworth et al, J. Pharmacol. Exp. Ther., 1999, 291, 1685-1691]. In murine models of pancreatitis-induced lung injury, pretreatment with a p38 MAPK inhibitor reduced TNF-α release in the airways and pulmonary edema [Denham et al, Crit. Care Med., 2000, 29, 628 and Yang et al, Surgery, 1999, 126, 216]. Inhibition of p38 MAPK before ovalbumin (OVA) challenge in OVA-sensitized mice decreased cytokine and inflammatory cell accumulation in the airways in an allergic airway model of inflammation, [Underwood et al, J. Pharmacol. Exp. Ther., 2000, 293, 281]. Increased activity of p38 MAP kinase has been observed in patients suffering from inflammatory bowel disease [Waetzig et al, J. Immunol, 2002, 168, 5432-5351]. p38 MAPK inhibitors have been shown to be efficacious in rat models of cardiac hypertrophy [Behr et al, Circulation, 2001, 104, 1292-1298] and cerebral focal ischemia [Barone et al, J. Pharmacol. Exp. Ther., 2001, 296, 312-321].

We have now discovered a group of compounds which are potent and selective inhibitors of p38 MAPK (p38α, β, γ and δ) and the isoforms and splice variants thereof especially p38α, p38β and p38β2. The compounds are thus of use in medicine, for example in the treatment and prophylaxis of immune and inflammatory disorders described herein. The compounds are characterised by the presence in the molecule of an α,α-disubstituted glycine motif or an α,α-disubstituted glycine ester motif which is hydrolysable by an intracellular carboxylesterase. Compounds of the invention having the lipophilic α,α-disubstituted glycine ester motif cross the cell membrane, and are hydrolysed to the acid by the intracellular carboxylesterases. The polar hydrolysis product accumulates in the cell since it does not readily cross the cell membrane. Hence the p38 MAP kinase activity of the compound is prolonged and enhanced within the cell. The compounds of the invention are related to the p38 MAP kinase inhibitors encompassed by the disclosures in International Patent Application WO03076405 but differ therefrom in that the present compounds have the amino acid ester motif referred to above.

The compounds of the invention are also related to those disclosed in our copending International Patent Application No. WO 2007/129040. The latter compounds have an α-monosubstituted glycine ester motif which also enables the compounds to cross the cell membrane into the cell where they are hydrolysed to the corresponding acid by intracellular carboxylesterases. However, that publication does not suggest that α,α-disubstituted glycine ester conjugates can be hydrolysed by intracellular carboxylesterases. In fact, it appears that the ability of the intracellular carboxyl esterases, principally hCE-1, hCE-2 and hCE-3, to hydrolyse α,α-disubstituted glycine esters has not previously been investigated.

The general concept of conjugating an α-mono substituted glycine ester motif to a modulator of an intracellular enzyme or receptor, to obtain the benefits of intracellular accumulation of the carboxylic acid hydrolysis product is disclosed in our International Patent Application WO 2006/117567. However, this publication does not suggest that α,α-disubstituted glycine ester conjugates can be hydrolysed by intracellular carboxylesterases. As mentioned above, it appears that the ability of the intracellular carboxyl esterases, principally hCE-1, hCE-2 and hCE-3, to hydrolyse α,α-disubstituted glycine esters has not previously been investigated.

DETAILED DESCRIPTION OF THE INVENTION

According to the invention there is provided a compound of formula (I):

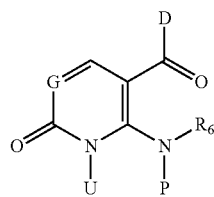

(I)

wherein:
G is —N= or —CH=
D is an optionally substituted divalent mono- or bicyclic aryl or heteroaryl radical having 5-13 ring members;
$R_6$ is hydrogen or optionally substituted $C_1$-$C_3$ alkyl;
P represents hydrogen and U represents a radical of formula (IA); or U represents hydrogen and P represents a radical of formula (IA);

(IA)

wherein
A represents an optionally substituted divalent mono- or bicyclic carbocyclic or heterocyclic radical having 5-13 ring members;
z is 0 or 1;
Y is a bond, —C(=O)—, —S(=O)$_2$—, —C(=O)NR$_7$—, —C(=S)—NR$_7$, —C(=NH)NR$_7$ or —S(=O)$_2$NR$_7$— wherein R$_7$ is hydrogen or optionally substituted $C_1$-$C_6$ alkyl;

$L^1$ is a divalent radical of formula -(Alk$^1$)$_m$(Q)$_n$(Alk$^2$)$_p$- wherein
m, n and p are independently 0 or 1,
Q is (i) an optionally substituted divalent mono- or bicyclic carbocyclic or heterocyclic radical having 5-13 ring members, or (ii), in the case where both m and p are 0, a divalent radical of formula —X$^2$-Q$^1$- or -Q$^1$-X$^2$— wherein X$^2$ is —O—, S— or NR$^A$— wherein R$^A$ is hydrogen or optionally substituted $C_1$-$C_3$ alkyl, and Q$^1$ is an optionally substituted divalent mono- or bicyclic carbocyclic or heterocyclic radical having 5-13 ring members,
Alk$^1$ and Alk$^2$ independently represent optionally substituted divalent $C_3$-$C_7$ cycloalkyl radicals, or optionally substituted straight or branched, $C_1$-$C_6$ alkylene, $C_2$-$C_6$ alkenylene, or $C_2$-$C_6$ alkynylene radicals which may optionally contain or terminate in an ether (—O—), thioether (—S—) or amino (—NR$^A$—) link wherein R$^A$ is hydrogen or optionally substituted $C_1$-$C_3$ alkyl; and
X$^1$ represents a bond; —C(=O); or —S(=O)$_2$—; —NR$_4$C(=O)—, —C(=O)NR$_4$—, —NR$_4$C(=O)NR$_5$—, —NR$_4$S(=O)$_2$—, or —S(=O)$_2$NR$_4$— wherein R$_4$ and R$_5$ are independently hydrogen or optionally substituted $C_1$-$C_6$ alkyl.
R$_1$ is a carboxylic acid group (—COOH), or an ester group which is hydrolysable by one or more intracellular esterase enzymes to a carboxylic acid group; and
R$_2$ and R$_3$ are selected from the side chains of a natural or non-natural alpha-amino acid, provided that neither R$_2$ or R$_3$ is hydrogen.

Compounds of formula (I) above may be prepared in the form of salts, especially pharmaceutically acceptable salts, N-oxides, hydrates, and solvates thereof. Any claim to a compound herein, or reference herein to "compounds of the invention", "compounds with which the invention is concerned", "compounds of formula (I)" and the like, includes salts, N-oxides, hydrates, and solvates of such compounds.

Although the above definition potentially includes molecules of high molecular weight, it is preferable, in line with general principles of medicinal chemistry practice, that the compounds with which this invention is concerned should have molecular weights of no more than 600.

In another broad aspect the invention provides the use of a compound of formula (I) as defined above, or an N-oxide, salt, hydrate or solvate thereof in the preparation of a composition for inhibiting the activity of p38 MAP kinase enzyme.

The compounds with which the invention is concerned may be used for the inhibition of p38 MAP kinase enzyme activity in vitro or in vivo.

In one aspect of the invention, the compounds of the invention may be used in the preparation of a composition for the treatment of autoimmune or inflammatory disease, particularly those mentioned above in which p38 MAP kinase activity plays a role.

In another aspect, the invention provides a method for the treatment of the foregoing disease types, which comprises administering to a subject suffering such disease an effective amount of a compound of formula (I) as defined above.

Terminology

The term "ester" or "esterified carboxyl group" means a group R$^X$O(C=O)— in which R$^x$ is the group characterising the ester, notionally derived from the alcohol R$^X$OH.

As used herein, the term "(C$_a$-C$_b$)alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

As used herein the term "divalent ($C_a$-$C_b$)alkylene radical" wherein a and b are integers refers to a saturated hydrocarbon chain having from a to b carbon atoms and two unsatisfied valences.

As used herein the term "($C_a$-$C_b$)alkenyl" wherein a and b are integers refers to a straight or branched chain alkenyl moiety having from a to b carbon atoms having at least one double bond of either E or Z stereochemistry where applicable. The term includes, for example, vinyl, allyl, 1- and 2-butenyl and 2-methyl-2-propenyl.

As used herein the term "divalent ($C_a$-$C_b$)alkenylene radical" means a hydrocarbon chain having from a to b carbon atoms, at least one double bond, and two unsatisfied valences.

As used herein the term "($C_a$-$C_b$)alkynyl" wherein a and b are integers refers to straight chain or branched chain hydrocarbon groups having from a to b carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "divalent ($C_a$-$C_b$)alkynylene radical" wherein a and b are integers refers to a divalent hydrocarbon chain having from a to b carbon atoms, and at least one triple bond.

As used herein the term "carbocyclic" refers to a mono-, bi- or tricyclic radical or a bridged monocyclic radical (for example bicyclo[2.2.1]hept-2-yl), having up to 16 ring atoms all of which are carbon, and includes aryl and cycloalkyl.

As used herein the term "cycloalkyl" refers to a monocyclic saturated carbocyclic radical having from 3-8 carbon atoms and includes, for example, cyclopropyl, cyclobutyl, cyclopentyl, cyclohexyl, cycloheptyl and cyclooctyl.

As used herein the unqualified term "aryl" refers to a mono-, bi- or tri-cyclic carbocyclic aromatic radical, and includes radicals having two monocyclic carbocyclic aromatic rings which are directly linked by a covalent bond. Illustrative of such radicals are phenyl, biphenyl and napthyl.

As used herein the unqualified term "heteroaryl" refers to a mono-, bi- or tri-cyclic aromatic radical containing one or more heteroatoms selected from S, N and O, and includes radicals having two such monocyclic rings, or one such monocyclic ring and one monocyclic aryl ring, which are directly linked by a covalent bond. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in its non-aromatic meaning relates to a mono-, bi- or tri-cyclic non-aromatic radical or bridged monocyclic non-aromatic radical, containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

A "divalent phenylene, pyridiylene, pyrimidinylene, or pyrazinylene radical" is a benzene, pyridine, pyrimidine or pyrazine ring, with two unsatisfied valencies, and includes 1,3-phenylene, 1,4-phenylene, and the following:

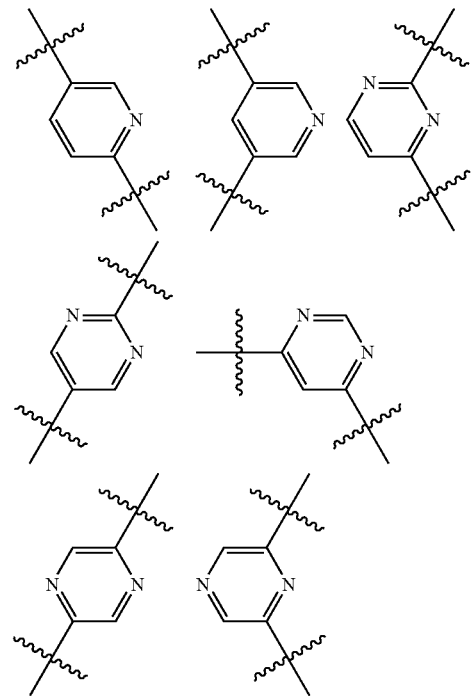

Unless otherwise specified in the context in which it occurs, the term "substituted" as applied to any moiety herein means substituted with up to four compatible substituents, each of which independently may be, for example, ($C_1$-$C_6$)alkyl, ($C_1$-$C_6$)alkoxy, hydroxy, hydroxy($C_1$-$C_6$)alkyl, mercapto, mercapto($C_1$-$C_6$)alkyl, ($C_1$-$C_6$)alkylthio, phenyl, halo (including fluoro, bromo and chloro), trifluoromethyl, trifluoromethoxy, nitro, nitrile (—CN), oxo, —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OH, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$, or —NR$^A$CONR$^A$R$^B$ wherein R$^A$ and R$^B$ are independently a ($C_1$-$C_6$)alkyl, ($C_3$-$C_6$)cycloalkyl, phenyl or monocyclic heteroaryl having 5 or 6 ring atoms, or R$^A$ and R$^B$ when attached to the same nitrogen atom form a cyclic amino group (for example morpholino, piperidinyl, piperazinyl, or tetrahydropyrrolyl). An "optional substituent" may be one of the foregoing substituent groups.

The term "side chain of a natural or non-natural alpha-amino acid" refers to the group R$^Y$ in a natural or non-natural amino acid of formula NH$_2$—OH(R$^Y$)—COOH.

Examples of side chains of natural alpha amino acids include those of alanine, arginine, asparagine, aspartic acid, cysteine, cystine, glutamic acid, histidine, 5-hydroxylysine, 4-hydroxyproline, isoleucine, leucine, lysine, methionine, phenylalanine, proline, serine, threonine, tryptophan, tyrosine, valine, α-aminoadipic acid, α-amino-n-butyric acid, 3,4-dihydroxyphenylalanine, homoserine, α-methylserine, ornithine, pipecolic acid, and thyroxine.

Natural alpha-amino acids which contain functional substituents, for example amino, carboxyl, hydroxy, mercapto, guanidyl, imidazolyl, or indolyl groups in their characteristic side chains include arginine, lysine, glutamic acid, aspartic acid, tryptophan, histidine, serine, threonine, tyrosine, and cysteine. When $R_2$ or $R_3$ in the compounds of the invention is one of those side chains, the functional substituent may optionally be protected.

The term "protected" when used in relation to a functional substituent in a side chain of a natural alpha-amino acid means a derivative of such a substituent which is substantially non-functional. For example, carboxyl groups may be esterified (for example as a $C_1$-$C_6$ alkyl ester), amino groups may be converted to amides (for example as a NHCOC$_1$-$C_6$ alkyl amide) or carbamates (for example as an NHC(=O)OC$_1$-$C_6$ alkyl or NHC(=O)OCH$_2$Ph carbamate), hydroxyl groups may be converted to ethers (for example an OC$_1$-$C_6$ alkyl or a O($C_1$-$C_6$ alkyl)phenyl ether) or esters (for example a OC(=O)C$_1$-$C_6$ alkyl ester) and thiol groups may be converted to thioethers (for example a tert-butyl or benzyl thioether) or thioesters (for example a SC(=O)C$_1$-$C_6$ alkyl thioester).

Examples of side chains of non-natural alpha amino acids include those referred to below in the discussion of suitable $R_2$ and $R_3$ groups for use in compounds of the present invention.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris(hydroxymethyl)amino-methane, L-arginine, L-lysine, N-ethyl piperidine, dibenzylamine and the like. Those compounds (I) which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesulfonic, glutamic, lactic, and mandelic acids and the like. For a review on suitable salts, see *Handbook of Pharmaceutical Salts: Properties, Selection, and Use* by Stahl and Wermuth (Wiley-VCH, Weinheim, Germany, 2002).

The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Compounds of the invention which contain one or more actual or potential chiral centres, because of the presence of asymmetric carbon atoms, can exist as enantiomers or as a number of diastereoisomers with R or S stereochemistry at each chiral centre. The invention includes all such enantiomers and diastereoisomers and mixtures thereof.

As mentioned, the esters of the invention are converted by intracellular esterases to the carboxylic acids. Both the esters and carboxylic acids may have p38 MAP kinase inhibitory activity in their own right. The compounds of the invention therefore include not only the ester, but also the corresponding carboxylic acid hydrolysis products.

In the compounds with which the invention is concerned, in any compatible combination, the following structural features may be present:

The Group D

D is an optionally substituted divalent mono- or bicyclic aryl or heteroaryl radical having 5-13 ring members. At present it is preferred that D be optionally substituted phenyl or optionally substituted pyridinyl. Optional substituents have been referred to above, but preferred optional substituents in D include fluoro and chloro, for example when D is 2,4-difluorophenyl.

P/U Regioisomers

Presently it is preferred that P be hydrogen and U be a radical of formula (IA) as defined above.

The Radical A

In the radical of formula (IA), it is currently preferred that A be optionally substituted 1,4 phenylene. In that case optional substituents have been referred to above, but preferred optional substituents include fluoro and chloro. A may also be, for example, any of the following, similarly optionally substituted:

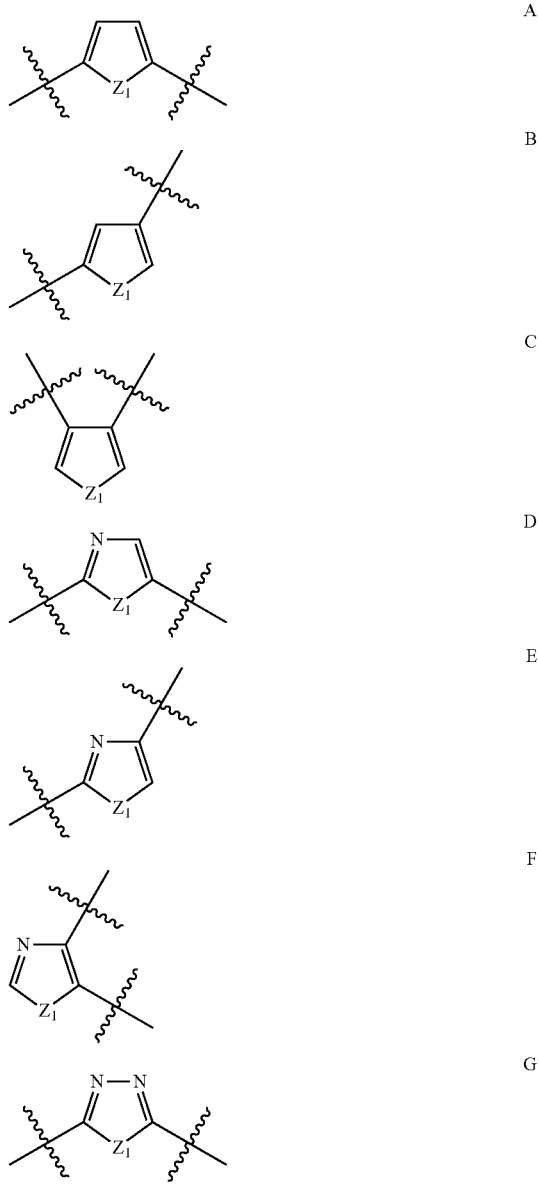

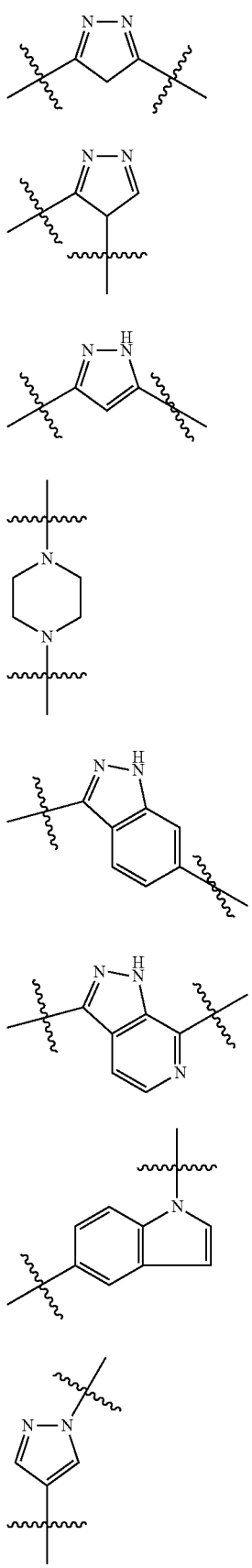
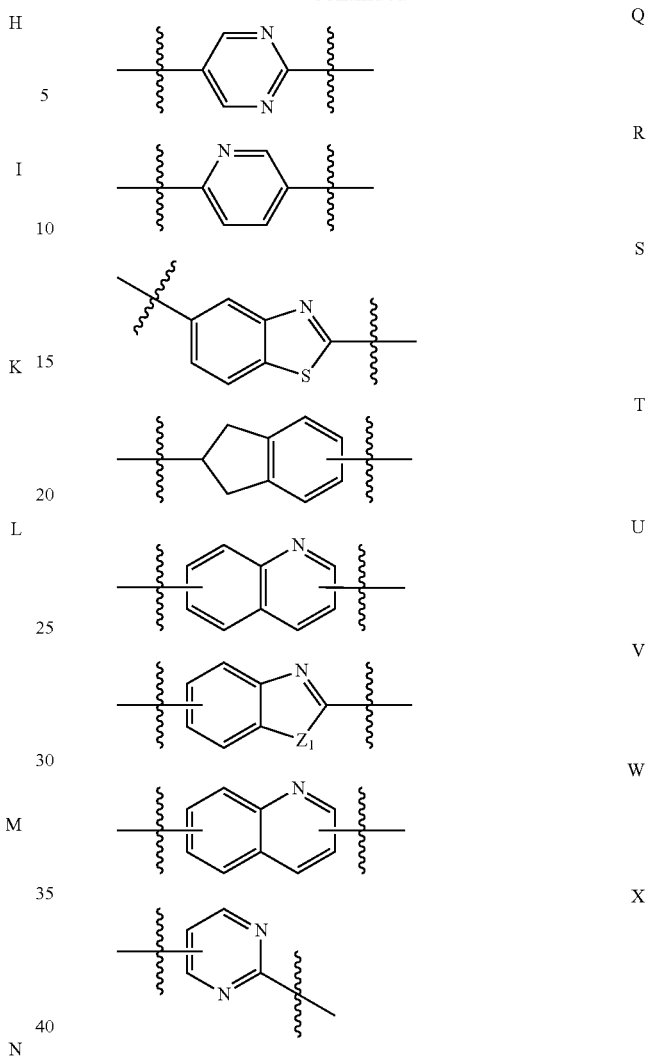
wherein $Z_1$ is NH, S or O.
A particularly preferred sub-group of compounds of the invention consists of those of formula (II):
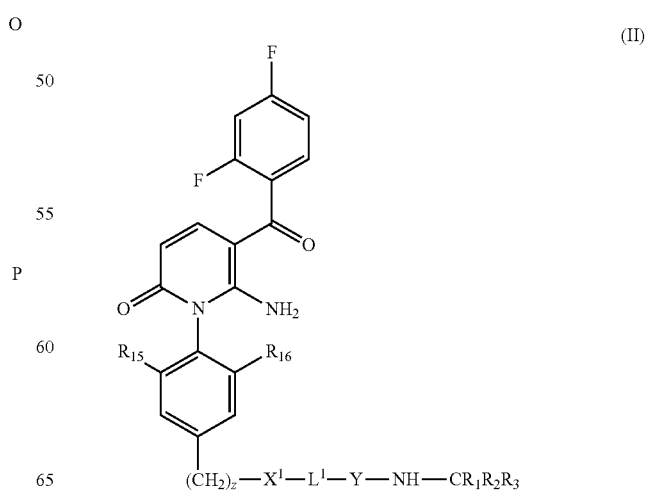

wherein $R_{15}$ and $R_{16}$ are independently hydrogen or fluoro, and wherein z, $X^1$, $L^1$, Y, $R^1$, $R^2$ and $R^3$ are as defined above with reference to formula (I), and as further discussed below.

The radical —Y-$L^1$-$X^1$—$[CH_2]_z$—

This radical (or bond) arises from the particular chemistry strategy chosen to link the amino acid ester motif $R_1R_2R_3CNH$— to the ring system A. Clearly the chemistry strategy for that coupling may vary widely, and thus many combinations of the variables Y, $L^1$, $X^1$ and z are possible. The precise combination of variables making up the linking chemistry between the amino acid ester motif and the ring system A will often be irrelevant to the primary binding mode of the compound as a whole. On the other hand, that linkage chemistry will in some cases pick up additional binding interactions with the enzyme. It should also be noted that the benefits of the amino acid ester motif (facile entry into the cell, esterase hydrolysis within the cell, and accumulation within the cell of active carboxylic acid hydrolysis product) are best achieved when the linkage between the amino acid ester motif and the ring system A is not a substrate for peptidase activity within the cell, which might result in cleavage of the amino acid from the molecule. Of course, stability to intracellular peptidases is easily tested by incubating the compound with disrupted cell contents, and analysing for any such cleavage.

With the foregoing general observations in mind, taking the variables making up the radical —Y-$L^1$-$X^1$—$[CH_2]_z$— in turn:

z may be 0 or 1, so that a methylene radical linked to the ring system A is optional;

specific preferred examples of Y when macrophage selectivity is not required include —(C=O)—, —(C=O)NH—, and —(C=O)O—; Where macrophage selectivity is required any of the other options for Y, including the case where Y is a bond, are appropriate.

In the radical $L^1$, examples of $Alk^1$ and $Alk^2$ radicals, when present, include —$CH_2$—, —$CH_2CH_2$—, —$CH_2CH_2CH_2$—, —$CH_2CH_2CH_2CH_2$—, —CH=CH—, —CH=CHCH$_2$—, —$CH_2$CH=CH—, $CH_2$CH=CHCH$_2$—, —C≡C—, —C≡CCH$_2$—, —$CH_2$C≡C—, and $CH_2$C≡CCH$_2$. Additional examples of $Alk^1$ and $Alk^2$ include —$CH_2$W—, —$CH_2CH_2$W—, —$CH_2CH_2$WCH$_2$—, —$CH_2CH_2$WCH(CH$_3$)—, —$CH_2$WCH$_2CH_2$—, —$CH_2$WCH$_2CH_2$WCH$_2$— and —WCH$_2$CH$_2$— where W is —O—, —S—, —NH—, —N(CH$_3$)—, or —$CH_2CH_2$N(CH$_2$CH$_2$OH)CH$_2$—. Further examples of $Alk^1$ and $Alk^2$ include divalent cyclopropyl, cyclopentyl and cyclohexyl radicals.

In $L^1$, when n is 0, the radical is a hydrocarbon chain (optionally substituted and perhaps having an ether, thioether or amino linkage). Presently it is preferred that there be no optional substituents in $L^1$. When both m and p are 0, $L^1$ is a divalent mono- or bicyclic carbocyclic or heterocyclic radical with 5-13 ring atoms (optionally substituted). When n is 1 and at least one of m and p is 1, $L^1$ is a divalent radical including a hydrocarbon chain or chains and a mono- or bicyclic carbocyclic or heterocyclic radical with 5-13 ring atoms (optionally substituted). When present, Q may be, for example, a divalent phenyl, naphthyl, cyclopropyl, cyclopentyl, or cyclohexyl radical, or a mono-, or bi-cyclic heterocyclic radical having 5 to 13 ring members, such as piperidinyl, piperazinyl, indolyl, pyridyl, thienyl, or pyrrolyl radical, but 1,4-phenylene is presently preferred.

Specifically, in some embodiments of the invention, $L^1$, m and p may be 0 with n being 1. In other embodiments, n and p may be 0 with m being 1. In further embodiments, m, n and p may be all 0. In still further embodiments m may be 0, n may be 1 with Q being a monocyclic heterocyclic radical, and p may be 0 or 1. $Alk^1$ and $Alk^2$, when present, may be selected from —$CH_2$—, —$CH_2CH_2$—, —$CH_2CH_2CH_2$—, —$CH_2$O—, —$CH_2CH_2$O—, —$CH_2$OCH$_2$—, —$CH_2CH_2$OCH$_2$—, and Q may be 1,4-phenylene.

Specific examples of the radical —Y-$L^1$-$X^1$—$[CH_2]$— include —C(=O)— and —C(=O)NH— as well as —$(CH_2)_v$—, —$(CH_2)_v$O—, —C(=O)—$(CH_2)_v$—, —C(=O)—$(CH_2)_v$O—, —C(=O)—NH—$(CH_2)_w$—, —C(=O)—NH—$(CH_2)_w$O—

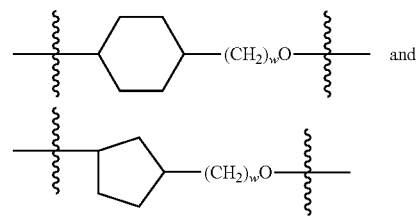

wherein v is 1, 2, 3 or 4 and w is 1, 2 or 3, such as —Y-$L^1$-$X^1$—$[CH_2]_z$—, is —$CH_2$—, —$CH_2CH_2$—, —$CH_2CH_2CH_2$—, —$CH_2CH_2CH_2CH_2$—, —$CH_2$O—, —$CH_2CH_2$O—, —$CH_2CH_2CH_2$O—, —$CH_2CH_2CH_2CH_2$O—, —C(=O)—$CH_2$—, —C(=O)—$CH_2$O—, —C(=O)—NH—$CH_2$—, or —C(=O)—NH—$CH_2$O—.

The Group $R_1$

In one class of compounds of the invention, $R_1$ is a carboxylic acid group. Although compounds of this class may be administered as the carboxylic acid or a salt thereof, it is preferred that they be generated in the cell by the action of an intracellular esterase on a corresponding compound in which $R_1$ is an ester group.

The ester group $R_1$ must be one which in the compound of the invention is hydrolysable by one or more intracellular carboxylesterase enzymes to a carboxylic acid group. Intracellular carboxylesterase enzymes capable of hydrolysing the ester group of a compound of the invention to the corresponding acid include the three known human enzyme isotypes hCE-1, hCE-2 and hCE-3. Although these are considered to be the main enzymes, other enzymes such as biphenylhydrolase (BPH) may also have a role in hydrolysing the ester. In general, if the carboxylesterase hydrolyses the free amino acid ester to the parent acid it will also hydrolyse the ester motif when covalently conjugated to the inhibitor. Hence, the broken cell assay and/or the isolated carboxylesterase assay described herein provide a straightforward, quick and simple first screen for esters which have the required hydrolysis profile. Ester motifs selected in that way may then be re-assayed in the same carboxylesterase assay when conjugated to the inhibitor via the chosen conjugation chemistry, to confirm that it is still a carboxylesterase substrate in that background.

Subject to the requirement that they be hydrolysable by intracellular carboxylesterase enzymes, examples of particular ester groups $R_1$ include those of formula —(C=O)O$R_{14}$ wherein $R_{14}$ is $R_8R_9R_{10}$C— wherein (i) $R_8$ is hydrogen or optionally substituted $(C_1$-$C_3)$alkyl-$(Z^1)_a$-$[(C_1$-$C_3)$alkyl]$_b$— or $(C_2$-$C_3)$alkenyl-$(Z^1)_a$-$[(C_1$-$C_3)$alkyl]$_b$- wherein a and b are independently 0 or 1 and $Z^1$ is —O—, —S—, or —NR$_{11}$— wherein R$_{11}$ is hydrogen or (C$_1$-C$_3$)alkyl; and R$_9$ and R$_{10}$ are independently hydrogen or (C$_1$-C$_3$)alkyl-;

(ii) R$_8$ is hydrogen or optionally substituted R$_{12}$R$_{13}$N—(C$_1$-C$_3$)alkyl- wherein R$_{12}$ is hydrogen or (C$_1$-C$_3$)alkyl and R$_{13}$ is hydrogen or (C$_1$-C$_3$)alkyl; or R$_{12}$ and R$_{13}$ together with the nitrogen to which they are attached form an optionally substituted monocyclic heterocyclic ring of 5- or 6-ring atoms or bicyclic heterocyclic ring system of 8 to 10 ring atoms, and R$_9$ and R$_{10}$ are independently hydrogen or (C$_1$-C$_3$)alkyl-; or (iii) R$_8$ and R$_9$ taken together with the carbon to which they are attached form an optionally substituted monocyclic carbocyclic ring of from 3 to 7 ring atoms or bicyclic carbocyclic ring system of 8 to 10 ring atoms, or bridged monocyclic carbocyclic ring system of 7 to 10 ring atoms, and R$_{10}$ is hydrogen.

In cases (i), (ii) and (iii) above, "alkyl" includes fluoroalkyl.

Within these classes (i), (ii) and (iii), R$_{10}$ is often hydrogen. Specific examples of R$_{14}$ include methyl, trifluoromethyl, ethyl, n- or iso-propyl, n-, sec- or tert-butyl, cyclohexyl, allyl, bicyclo[2.2.1]hept-2-yl, 2,3-dihydro-1H-inden-2-yl, phenyl, benzyl, 2-, 3- or 4-pyridylmethyl, N-methylpiperidin-4-yl, tetrahydrofuran-3-yl or methoxyethyl. Currently preferred is where R$_{14}$ is cyclopentyl.

Macrophages are known to play a key role in inflammatory disorders through the release of cytokines in particular TNFα and IL-1 (van Roon et al, Arthritis and Rheumatism, 2003, 1229-1238). In rheumatoid arthritis they are major contributors to the maintenance of joint inflammation and joint destruction. Macrophages are also involved in tumour growth and development (Naldini and Carraro, Curr Drug Targets Inflamm Allergy, 2005, 3-8). Hence agents that selectively target macrophage cell proliferation could be of value in the treatment of cancer and autoimmune disease. Targeting specific cell types would be expected to lead to reduced side-effects. The inventors have discovered a method of targeting p38 kinase inhibitors to macrophages which is based on the observation that the way in which the esterase motif is linked to the p38 kinase inhibitor determines whether it is hydrolysed, and hence whether or not it accumulates in different cell types. Specifically it has been found that macrophages contain the human carboxylesterase hCE-1 whereas other cell types do not. In the general formula (I) when the nitrogen of the esterase motif R$_1$C(R$_2$)(R$_3$)NH— is not directly linked to a carbonyl (—C(=O)—), ie when Y is not a —C(=O), —C(=O)O— or —C(=O)NR$_3$— radical, the ester will only be hydrolysed by hCE-1 and hence the inhibitors will only accumulate in macrophages. Herein, unless "monocyte" or "monocytes" is specified, the term macrophage or macrophages will be used to denote macrophages (including tumour associated macrophages) and/or monocytes.

Substituents R$_2$ and R$_3$

The substituents R$_2$ and R$_3$ may be regarded as the α-substituents of an α,α-disubstituted glycine or an α,α-disubstituted glycine ester. These substituents may therefore be the side chains of a natural or non-natural alpha-amino acid other than glycine, and in such side chains any functional groups may be protected.

For example, examples of R$_2$ and R$_3$ include phenyl and groups of formula —CR$_a$R$_b$R$_c$ in which:

each of R$_a$, R$_b$ and R$_c$ is independently hydrogen, (C$_1$-C$_6$)alkyl, (C$_2$-C$_6$)alkenyl, (C$_2$-C$_6$)alkynyl, phenyl(C$_1$-C$_6$)alkyl, (C$_3$-C$_8$)cycloalkyl; or R$_c$ is hydrogen and R$_a$ and R$_b$ are independently phenyl or heteroaryl such as pyridyl; or R$_c$ is hydrogen, (C$_1$-C$_6$)alkyl, (C$_2$-C$_6$)alkenyl, (C$_2$-C$_6$)alkynyl, phenyl(C$_1$-C$_6$)alkyl, or (C$_3$-C$_8$)cycloalkyl, and R$_a$ and R$_b$ together with the carbon atom to which they are attached form a 3 to 8 membered cycloalkyl or a 5- to 6-membered heterocyclic ring; or R$_a$, R$_b$ and R$_c$ together with the carbon atom to which they are attached form a tricyclic ring (for example adamantyl); or R$_a$ and R$_b$ are each independently (C$_1$-C$_6$)alkyl, (C$_2$-C$_6$)alkenyl, (C$_2$-C$_6$)alkynyl, phenyl(C$_1$-C$_6$)alkyl, or a group as defined for R$_c$ below other than hydrogen, or R$_a$ and R$_b$ together with the carbon atom to which they are attached form a cycloalkyl or heterocyclic ring, and R$_c$ is hydrogen, —OH, —SH, halogen, —CN, —CO$_2$H, (C$_1$-C$_4$)perfluoroalkyl, —CH$_2$OH, —O(C$_1$-C$_6$)alkyl, —O(C$_2$-C$_6$)alkenyl, —S(C$_1$-C$_6$)alkyl, —SO(C$_1$-C$_6$)alkyl, —SO$_2$(C$_1$-C$_6$) alkyl, —S(C$_2$-C$_6$)alkenyl, —SO(C$_2$-C$_6$)alkenyl, —SO$_2$(C$_2$-C$_6$)alkenyl or a group -Q-W wherein Q represents a bond or —O—, —S—, —SO— or —SO$_2$— and W represents a phenyl, phenylalkyl, (C$_3$-C$_8$)cycloalkyl, (C$_3$-C$_8$)cycloalkylalkyl, (C$_4$-C$_8$)cycloalkenyl, (C$_4$-C$_8$)cycloalkenylalkyl, heteroaryl or heteroarylalkyl group, which group W may optionally be substituted by one or more substituents independently selected from, hydroxyl, halogen, —CN, —CONH$_2$, —CONH(C$_1$-C$_6$)alkyl, —CONH(C$_1$-C$_6$alkyl)$_2$, —CHO, —CH$_2$OH, (C$_1$-C$_4$ perfluoroalkyl, —O(C$_1$-C$_6$)alkyl, —S(C$_1$-C$_6$)alkyl, —SO(C$_1$-C$_6$)alkyl, —SO$_2$(C$_1$-C$_6$)alkyl, —NO$_2$, —NH$_2$, —NH(C$_1$-C$_6$)alkyl, —N((C$_1$-C$_6$)alkyl)$_2$, —NHCO(C$_1$-C$_6$)alkyl, (C$_1$-C$_6$)alkyl, (C$_2$-C$_6$)alkenyl, (C$_2$-C$_6$)alkynyl, (C$_3$-C$_8$)cycloalkyl, (C$_4$-C$_8$)cycloalkenyl, phenyl or benzyl.

Alternatively, the substituents R$_2$ and R$_3$, taken together with the carbon to which they are attached, may form a 3-6 membered saturated spiro cycloalkyl ring, such as a cyclopropyl, cyclopentyl or cyclohexyl ring or spiro heterocyclyl ring such as a piperidin-4-yl ring.

In some cases, at least one of the substituents R$_2$ and R$_3$ is a C$_1$-C$_6$ alkyl substituent, for example methyl, ethyl, or n- or iso-propyl.

In some embodiments, one of the substituents R$_2$ and R$_3$ is a C$_1$-C$_6$ alkyl substituent, for example methyl, ethyl, or n- or iso-propyl, and the other is selected from the group consisting of methyl, ethyl, n- and iso-propyl, n-, sec- and tert-butyl, phenyl, benzyl, thienyl, cyclohexyl, and cyclohexylmethyl.

Currently preferred are cases where one of R$_2$ and R$_3$ is methyl. and the other is methyl, ethyl, or n- or iso-propyl; or where R$_2$ and R$_3$ taken together with the carbon to which they are attached form a cyclopropyl, cyclobutyl, cyclopentyl or cyclohexyl ring. In a particular case, the substituents R$_2$ and R$_3$ are each methyl.

For compounds of the invention which are to be administered systemically, esters with a slow rate of carboxylesterase cleavage are preferred, since they are less susceptible to pre-systemic metabolism. Their ability to reach their target tissue intact is therefore increased, and the ester can be converted inside the cells of the target tissue into the acid product. However, for local administration, where the ester is either directly applied to the target tissue or directed there by, for example, inhalation, it will often be desirable that the ester has a rapid rate of esterase cleavage, to minimise systemic exposure and consequent unwanted side effects. In the compounds of this invention, if the carbon adjacent to the alpha carbon of the alpha amino acid ester ester is monosubstituted, ie R$_2$ is CH$_2$R$^z$ (R$^z$ being the mono-substituent) then the esters tend to be cleaved more rapidly than if that carbon is di- or tri-substituted, as in the case where $R_2$ is, for example, phenyl or cyclohexyl.

As mentioned above, the compounds with which the invention is concerned are inhibitors of p38 MAK kinase activity, and are therefore of use in the treatment of diseases such as psoriasis, inflammatory bowel disease, Crohns disease, ulcerative colitis, chronic obstructive pulmonary disease, asthma, multiple sclerosis, diabetes, atopic dermatitis, graft versus host disease, or systemic lupus erythematosus and rheumatoid arthritis, in which p38 MAP kinase activity plays a part.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application by inhalation, the drug may be formulated for aerosol delivery for example, by pressure-driven jet atomizers or ultrasonic atomizers, or preferably by propellant-driven metered aerosols or propellant-free administration of micronized powders, for example, inhalation capsules or other "dry powder" delivery systems. Excipients, such as, for example, propellants (e.g. Frigen in the case of metered aerosols), surface-active substances, emulsifiers, stabilizers, preservatives, flavorings, and fillers (e.g. lactose in the case of powder inhalers) may be present in such inhaled formulations. For the purposes of inhalation, a large number of apparata are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described in European Patent Application EP 0 505 321).

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agent can be dissolved in the vehicle.

Synthesis

There are multiple synthetic strategies for the synthesis of the compounds (I) with which the present invention is concerned, but all rely on known chemistry, known to the synthetic organic chemist. Thus, compounds according to formula (I) can be synthesised according to procedures described in the standard literature and are well-known to those skilled in the art. Typical literature sources are "*Advanced organic chemistry*", 4$^{th}$ Edition (Wiley), J March, "*Comprehensive Organic Transformation*", 2$^{nd}$ Edition (Wiley), R. C. Larock, "*Handbook of Heterocyclic Chemistry*", 2$^{nd}$ Edition (Pergamon), A. R. Katritzky), review articles such as found in "*Synthesis*", "*Acc. Chem. Res.*", "*Chem. Rev*", or primary literature sources identified by standard literature searches online or from secondary sources such as "*Chemical Abstracts*" or "*Beilstein*".

The compounds of the invention may be prepared by a number of processes generally described below and more specifically in the Examples hereinafter. In the reactions described below, it may be necessary to protect reactive functional groups, for example hydroxyl, amino and carboxy groups, where these are desired in the final product, to avoid their unwanted participation in the reactions [see for example Greene, T. W., "Protecting Groups in Organic Synthesis", John Wiley and Sons, 1999]. Conventional protecting groups may be used in conjunction with standard practice. In some instances deprotection may be the final step in the synthesis of a compound of general formula (I) and the processes according to the invention described herein after are understood to extend to such removal of protecting groups.

The compounds of the invention may be prepared according to the following Examples. All temperatures are in ° C. The following abbreviations are used:

EtOAc=ethyl acetate
Boc=tert-butoxycarbonyl
CDI=1,1'-carbonyl diimidazole
DCM=dichloromethane
DMAP=dimethylaminopyridine
DMF=dimethylformamide
DMSO=dimethyl sulfoxide
NMP=1-methyl-2-pyrrolidinone
THF=tetrahydrofuran
HCl=hydrochloric acid NaHCO$_3$=sodium hydrogen carbonate
Pd/C=palladium on carbon
MgSO$_4$=magnesium sulfate
EDCl=N-(3-Dimethylaminopropyl)-N'-ethylcarbodiimide hydrochloride
Et$_2$O=diethyl ether
HOBt=1-hydroxybenzotriazole
TFA=trifluoroacetic acid
TLC=thin layer chromatography
ml=milliliter(s)
g=gram(s)
mg=milligram(s)
mol=moles
mmol=millimole(s)
LCMS=high performance liquid chromatography/mass spectrometry
NMR=nuclear magnetic resonance
RT=room temperature Microwave irradiation was carried out using a CEM Discover focused microwave reactor. Solvents were removed using a GeneVac Series I without heating or a Genevac Series II with VacRamp at 30° C. or a Buchi rotary evaporator. Purification of compounds by flash chromatography column was performed using silica gel, particle size 40-63 µm (230-400 mesh) obtained from Silicycle. Purification of compounds by preparative HPLC was performed on Gilson systems using reverse phase ThermoHypersil-Keystone Hyperprep HS C18 columns (12 µm, 100×21.2 mm), gradient 20-100% B (A=water/0.1% TFA, B=acetonitrile/0.1% TFA) over 9.5 min, flow=30 ml/min, injection solvent 2:1 DMSO: acetonitrile (1.6 ml), UV detection at 215 nm.

$^1$H NMR spectra were recorded on a Bruker 400 MHz AV or a Bruker 300 MHz AV spectrometer in deuterated solvents. Chemical shifts (δ) are in parts per million. Thin-layer chromatography (TLC) analysis was performed with Kieselgel 60 F$_{254}$ (Merck) plates and visualized using UV light.

Analytical LCMS was performed on Agilent HP1100, Waters 600 or Waters 1525 LC systems using reverse phase Hypersil BDS C18 columns (5 µm, 2.1×50 mm), gradient 0-95% B (A=water/0.1% TFA, B=acetonitrile/0.1% TFA) over 2.10 min, flow=1.0 ml/min. UV spectra were recorded at 215 nm using a Gilson G1315A Diode Array Detector, G1214A single wavelength UV detector, Waters 2487 dual wavelength UV detector, Waters 2488 dual wavelength UV detector, or Waters 2996 diode array UV detector. Mass spectra were obtained over the range m/z 150 to 850 at a sampling rate of 2 scans per second or 1 scan per 1.2 seconds using Micromass LCT with Z-spray interface or Micromass LCT with Z-spray or MUX interface. Data were integrated and reported using OpenLynx and OpenLynx Browser software.

Intermediate 1: 4-chlorophenyl 3-(2,4-difluorophenyl)-3-oxopropanimidothioate

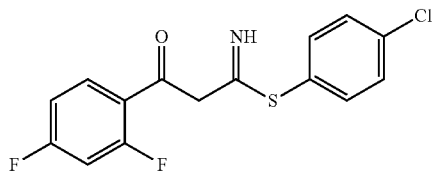 [SMILES: N=C(CC(=O)c1ccc(F)cc1F)Sc1ccc(Cl)cc1]

Intermediate 1 can be prepared using experimental procedures described in WO 2003076405.

Intermediate 2: {4-[6-amino-5-(2,4-difluorobenzoyl-2-oxopyridin-1(2H)yl]-phenyl}acetaldehyde

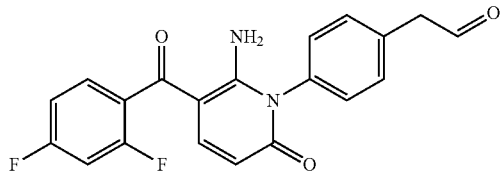 [SMILES: Nc1c(C(=O)c2ccc(F)cc2F)ccc(=O)n1-c1ccc(CC=O)cc1]

{4-[6-Amino-5-(2,4-difluorobenzoyl)-2-oxopyridin-1(2H)yl]-phenyl}acetaldehyde was synthesised using the route shown in Scheme 1 below.

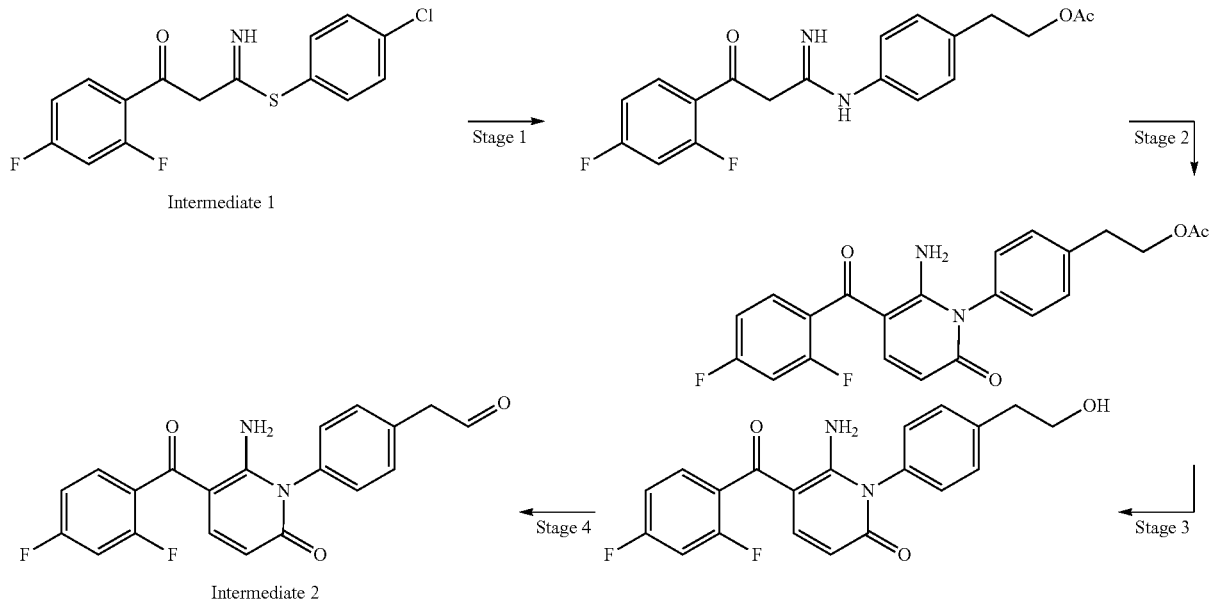

Scheme 1

Stage 1—2-(4-{[3-(2,4-difluorophenyl)-3-oxopropanimidoyl]amino}phenyl)ethyl acetate 4-chlorophenyl 3-(2,4-difluorophenyl)-3-oxopropanimidothioate (Intermediate 1) (69.7 g, 192 mmol) was suspended in glacial acetic acid (700 ml) and 2-(4-aminophenyl)ethanol (27.71 g, 202 mmol, 1.05 eq) was added. The mixture was heated at 80° C. for 2.5 hours before being allowed to cool to room temperature and concentrated under reduced pressure. The residue was triturated with $Et_2O$ (500 ml) and washed with $Et_2O$ (2×250 ml) to give a white solid, which was suspended in saturated $NaHCO_3$ (700 ml) and stirred vigorously for 30 minutes. Filtration and washing with water afforded a beige solid which was dried under reduced pressure to give the title compound (64.12 g, 92% yield).

LC/MS: m/z 361 $[M+H]^+$. $^1H$ NMR (300 MHz, DMSO-$d_6$) δ: 7.79-7.71 (1H, m), 7.45-7.07 (6H, m), 5.26 (1H, s), 4.21 (2H, t, J=6.8 Hz), 2.89 (2H, t, J=6.5 Hz), 2.00 (3H, s).

Stage 2—2-{4-[6-amino-5-(2,4-difluorobenzoyl)-2-oxopyridin-1(2H)-yl]phenyl}ethyl acetate CDI (43.26 g, 267 mmol, 1.5 eq) was dissolved in anhydrous THF (1 l) under an atmosphere of nitrogen and cooled to 0° C. Propiolic acid (16.43 ml, 267 mmol, 1.5 eq) was added dropwise and the mixture allowed to warm to room temperature and stirred for 1 hour. A suspension of 2-(4-{[3-(2,4-difluorophenyl)-3-oxopropanimidoyl]-amino}phenyl) ethyl acetate (64.12 g, 178 mmol) in anhydrous THF (500 ml) was added and the mixture heated at 80° C. for 6 hours before being left to stir at room temperature overnight. The resulting precipitate was collected by filtration, washed with $Et_2O$ and dried under reduced pressure to give the title compound as a pale yellow solid (39.56 g). The filtrate was concentrated under reduced pressure to give a brown oil that was triturated with EtOAc (500 ml), providing a second batch of product by filtration (7.21 g). The two batches were combined to afford the title compound as a yellow solid (46.77 g, 64% yield).

LC/MS: m/z 413 $[M+H]^+$. $^1H$ NMR (300 MHz, DMSO-$d_6$) δ: 7.55-7.37 (4H, m), 7.3-7.20 (4H, m), 5.72 (1H, d, J=9.6 Hz), 4.30 (2H, t, J=6.9 Hz), 3.01 (2H, t, J=6.9 Hz), 2.04 (3H, s).

Stage 3—6-amino-5-(2,4-difluorobenzoyl)-1-[4-(2-hydroxyethyl)phenyl]pyridin-2(1H)-one 2-{4-[6-amino-5-(2,4-difluorobenzoyl)-2-oxopyridin-1 (2H)-yl]phenyl}ethyl acetate (46.77 g, 113 mmol) was suspended in 6N aqueous HCl (500 ml) and heated at reflux for 2 hours. A precipitate formed upon cooling to room temperature which was collected by filtration, suspended in saturated aqueous $NaHCO_3$ (1000 ml) and stirred vigorously for 30 minutes. Filtration, washing with water (2×500 ml) and drying under reduced pressure afforded the title compound as an off-white solid (40.11 g, 96% yield).

LC/MS: m/z 371 $[M+H]^+$. $^1H$ NMR (300 MHz, DMSO-$d_6$) δ: 7.55-7.37 (4H, m), 7.31-7.20 (4H, m), 5.71 (1H, d, J=9.9 Hz), 4.69 (1H, t, J=5.3 Hz), 3.71 (2H, m), 2.84 (2H, d, J=6.9 Hz).

Stage 4—{4-[6-amino-5-(2,4-difluorobenzoyl)-2-oxopyridin-1(2H)-yl]phenyl}-acetaldehyde To a suspension of 6-amino-5-(2,4-difluorobenzoyl)-1-[4-(2-hydroxyethyl)phenyl]-pyridin-2(1H)-one (15.00 g, 40.5 mmol) in anhydrous DCM (750 ml) at 0° C. was added Dess-Martin Periodinane (20.62 g, 48.6 mmol, 1.2 eq) in portions. The mixture was allowed to warm to room temperature and stirred for 3 hours, before being poured into saturated aqueous $NaHCO_3$ (400 ml) and saturated aqueous $Na_2S_2O_3$ (400 ml) and stirred vigorously for 30 minutes. The aqueous layer was separated and extracted with DCM (2×500 ml), and the organic extracts combined and dried over $MgSO_4$. Filtration and concentration under reduced pressure afforded the title compound as a crude pale yellow solid that was used without further purification (15.13 g).

LC/MS: m/z 369 $[M+H]^+$.

Intermediate 3: 2-(4-Amino-3,5-difluoro-phenyl)-ethanol

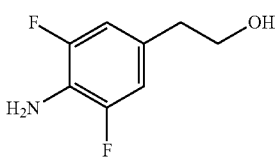 [SMILES: Nc1c(F)cc(CCO)cc1F]

2-(4-Amino-3,5-difluoro-phenyl)-ethanol was synthesised using the route shown in Scheme 2 below.

Scheme 2

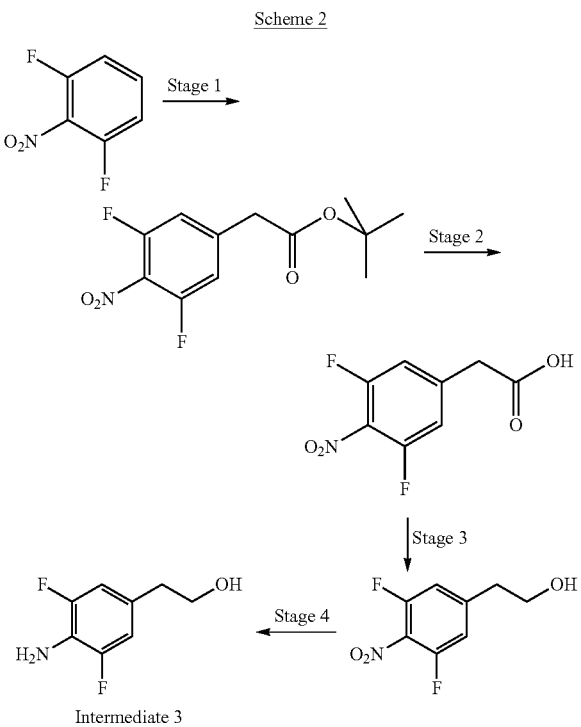

Intermediate 3

Stage 1—tert-butyl (3,5-difluoro-4-nitrophenyl)acetate

A mixture of potassium tert-butoxide (12.3 g, 111.0 mmol) in NMP (100 ml) was cooled to −20° C. under $N_2$. A mixture of 2,6-difluoronitrobenzene (5.0 g, 31.43 mmol) and tert-butylchloroacetate (7.6 ml, 53.11 mmol) in NMP (100 ml) was added slowly at −10° C. to −20° C. over 1.5 hours. After 1.5 hours the reaction was quenched by pouring into 2M HCl (120 ml) and ice, then heptane (300 ml) was added. The mixture was stirred for 10 minutes, separated and the aqueous extracted with heptane (2×400 ml). The organic layer was washed with brine (×2), dried (MgSO$_4$), filtered and washed with heptane. The solution was concentrated in vacuo and the residue purified by column chromatography (3-4% EtOAc/Heptane) to provide the title compound as an orange oil (4.34 g, 53% yield).

$^1$H NMR (300 MHz, CDCl$_3$) δ: 7.06 (2H, d, J=8.7 Hz), 3.59 (2H, s), 1.48 (9H, s).

Stage 2—(3,5-difluoro-4-nitrophenyl)acetic acid

To a solution of tert-butyl (3,5-difluoro-4-nitrophenyl)acetate (4.34 g, 15.88 mmol) in DCM (10 ml), at 0° C., was added TFA (10 ml). The reaction was warmed to room temperature and stirred for 1.5 hours. The reaction was concentrated in vacuo, slurried in heptane (10 ml), filtered and dried to provide the title compound as an orange solid (2.95 g, 86% yield).

$^1$H NMR (300 MHz, d$_6$DMSO) δ: 7.45 (2H, d, J=9.6 Hz), 3.79 (2H, s).

Stage 3—2-(3,5-difluoro-4-nitrophenyl)ethanol

A solution of (3,5-difluoro-4-nitrophenyl)acetic acid (2.95 g, 13.59 mmol) in THF (30 ml), under N$_2$, was cooled to 0° C. and a solution of BH$_3$Me$_2$S in THF (10.2 ml, 20.38 mmol) was added dropwise over 5 minutes. The mixture was warmed to room temperature and stirred for 4.5 hours. The reaction was cooled to 0° C. and quenched with MeOH (10 ml). The mixture was concentrated in vacuo and the residue purified by column chromatography (30-60% EtOAc/Heptane) to provide the title compound as an oil (2.45 g, 89% yield).

$^1$H NMR (300 MHz, CDCl$_3$) δ: 7.03 (2H, d, J=9.3 Hz), 3.97-3.91 (2H, q, J=5.4, 5.7 Hz), 2.93 (2H, t, J=6.2 Hz), 1.52 (1H, t, J=5.0 Hz).

Stage 4—(4-amino-3,5-difluorophenyl)ethanol

To a solution of 2-(3,5-difluoro-4-nitrophenyl)ethanol (2.45 g, 12.06 mmol) in EtOAc (50 ml) was added Pd/C (0.8 g). The mixture was stirred under an atmosphere of H$_2$ for 19 hours, filtered and concentrated in vacuo to provide the title compound as a pale brown solid (2.15 g, 100% yield).

$^1$H NMR (300 MHz, CDCl$_3$) δ: 6.70-6.67 (2H, m), 3.82 (2H, t, J=6.5 Hz), 2.76 (2H, t, J=6.5 Hz).

Intermediate 4: {4-[6-amino-5-(2,4-difluoro-benzoyl)-2-oxo-2H-pyridin-1-yl]-3,5-difluoro-phenyl}-acetaldehyde

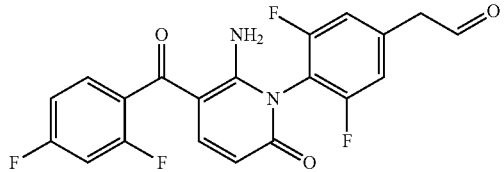 [SMILES: Nc1c(C(=O)c2ccc(F)cc2F)ccc(=O)n1-c1c(F)cc(CC=O)cc1F]

{4-[6-Amino-5-(2,4-difluoro-benzoyl)-2-oxo-2H-pyridin-1-yl]-3,5-difluoro-phenyl}-acetaldehyde was synthesised using the route shown in Scheme 3 below.

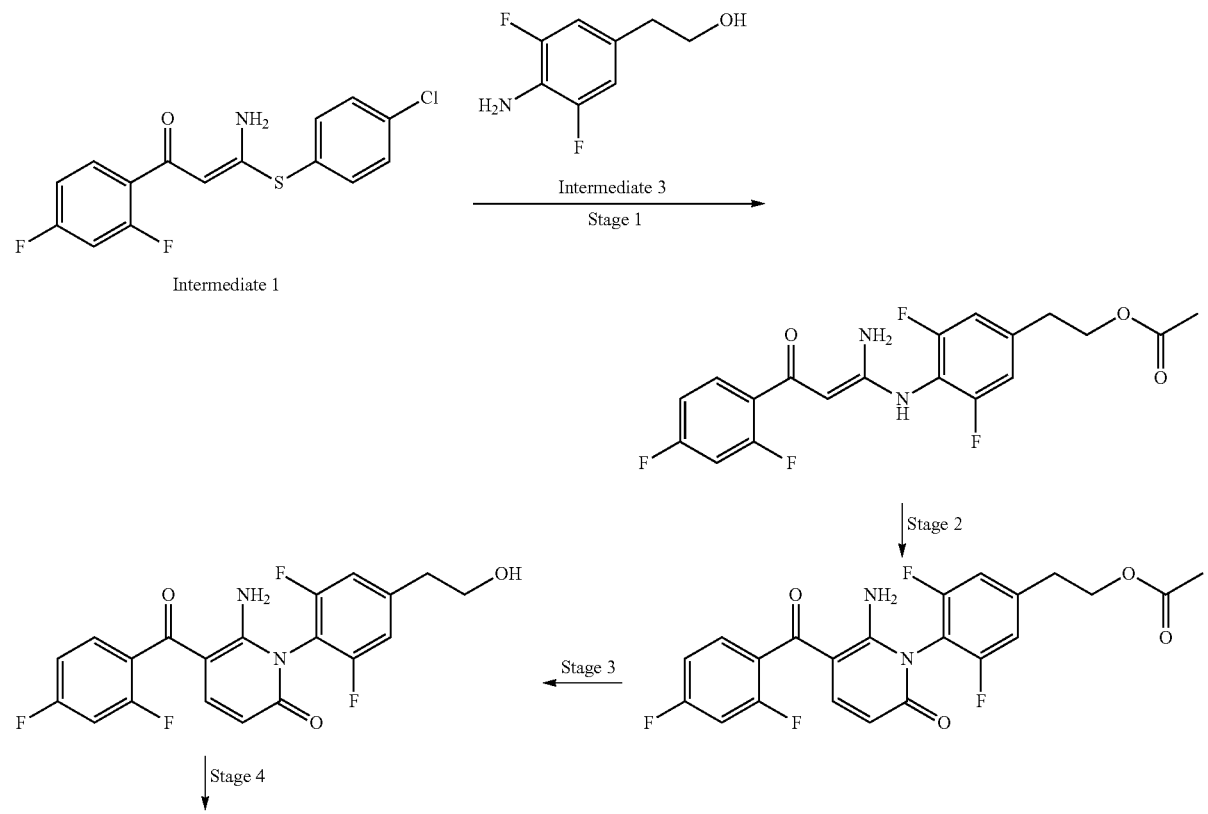

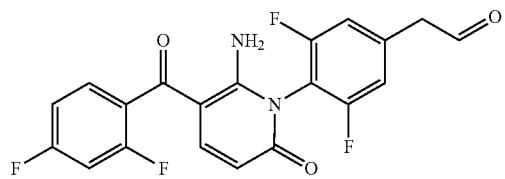

Intermediate 4

Stage 1—2-(4-{[1-amino-3-(2,4-difluorophenyl)-3-oxoprop-1-en-1-yl]amino}-3,5-difluorophenyl)ethyl acetate To a mixture of 3-amino-3-[(4-chlorophenyl)thio]-1-(2,4-difluorophenyl)prop-2-en-1-one hydrochloride (3.99 g, 11.1 mmol) (Intermediate 1) in acetic acid (20 ml) was added 2-(4-amino-3,5-difluorophenyl)ethanol (Intermediate 3) (2.00 g, 11.6 mmol) and the mixture heated at 80° C. for 20 hours. The mixture was cooled, concentrated in vacuo and the residue triturated in diethyl ether to provide a solid. The solid was partitioned between EtOAc and sat NaHCO₃, washed with brine, dried (MgSO₄) and concentrated in vacuo to provide the title compound as a solid (2.91 g, 67% yield).

LC/MS: m/z 397 [M+H]⁺.

Stage 2—2-{4-[6-amino-5-(2,4-difluorobenzoyl)-2-oxopyridin-1(2H)-yl]-3,5-difluorophenyl}ethyl acetate To a solution of CDI (1.78 g, 10.98 mmol) in THF (36 ml), under N₂ at 0° C., was added dropwise propiolic acid (675 µl, 10.98 mmol). The mixture was warmed to room temperature and stirred for 1.5 hours. A solution of 2-(4-{[1-amino-3-(2,4-difluorophenyl)-3-oxoprop-1-en-1-yl]amino}-3,5-difluorophenyl)ethyl acetate (2.9 g, 7.32 mmol) in THF (18 ml) was added dropwise and the mixture heated at 80° C. for 5 hours. The mixture was cooled, concentrated in vacuo and the residue purified twice by column chromatography (0.7-1% MeOH/DCM) to provide the title compound as a solid (1.20 g, 37% yield).

¹H NMR (300 MHz, CDCl₃) δ: 7.49-7.39 (2H, m), 7.09-6.90 (4H, m), 5.93 (1H, d, J=9.9 Hz), 4.37 (2H, t, J=6.4 Hz), 3.06 (2H, t, J=6.6 Hz), 2.10 (3H, s).

Stage 3—6-amino-5-(2,4-difluorobenzoyl)-1-[2,6-difluoro-4-(2-hydroxyethyl)phenyl]pyridin-2(1H)-one To a mixture of 2-{4-[6-amino-5-(2,4-difluorobenzoyl)-2-oxopyridin-1(2H)-yl]-3,5-difluorophenyl}ethyl acetate (1.1 g, 2.45 mmol) in 6N aq HCl (50 ml) was heated at reflux for 24 hours. The mixture was cooled, filtered and washed with water. The precipitate was partitioned between EtOAc and sat aq NaHCO₃, the organic layer further washed with brine, dried (MgSO₄) and concentrated in vacuo to provide the title compound as a solid (993 mg, 100% yield).

¹H NMR (300 MHz, CDCl₃) δ: 7.49-7.39 (2H, m), 7.15-6.90 (4H, m), 5.92 (1H, d, J=9.6 Hz), 4.00-3.85 (2H, m), 2.95 (2H, t, J=6.0 Hz).

Stage 4-{4-[6-amino-5-(2,4-difluorobenzoyl)-2-oxopyridin-1(2H)-yl]-3,5-difluorophenyl}acetaldehyde To a mixture of 6-amino-5-(2,4-difluorobenzoyl)-1-[2,6-difluoro-4-(2 hydroxyethyl)phenyl]pyridin-2(1H)-one (500 mg, 1.23 mmol) in DCM (20 ml) was added Dess-Martin periodinane (783 mg, 1.85 mmol). The mixture was stirred for 3.5 hours, sat aq Na₂S₂O₃ (20 ml) and sat NaHCO₃ (20 ml) was added and the mixture stirred vigorously for 30 minutes. The organic layer was separated and the aqueous extracted with DCM. The organic layer was washed with brine, dried (MgSO₄) and concentrated to provide the title compound as a solid (497 mg, 100% yield).

¹H NMR (300 MHz, CDCl₃) δ: 9.88 (1H, s), 7.49-7.40 (2H, m), 7.12-6.91 (4H, m), 5.93 (1H, d, J=9.9 Hz), 3.89 (2H, s).

Intermediate 5: {4-[6-amino-5-(2,4-difluorobenzoyl)-2-oxopyridin-1(2H)-yl]phenyl}acetic acid

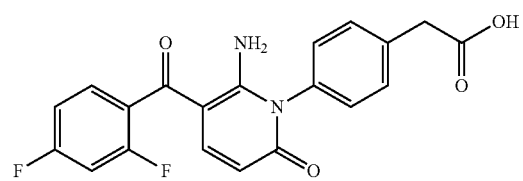 [SMILES: Nc1c(C(=O)c2ccc(F)cc2F)ccc(=O)n1-c1ccc(CC(=O)O)cc1]

Intermediate 5 was synthesised using the route shown in Scheme 4 below.

Scheme 4

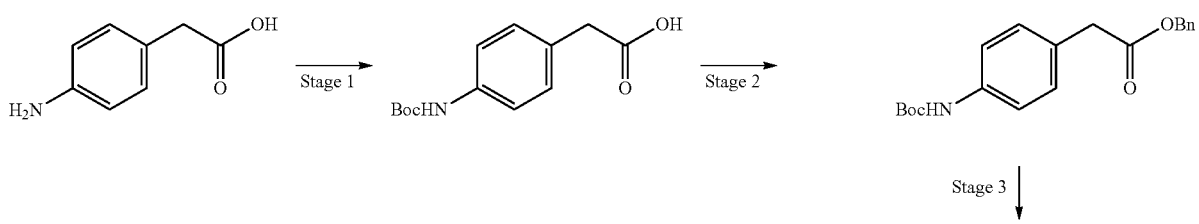

Stage 3

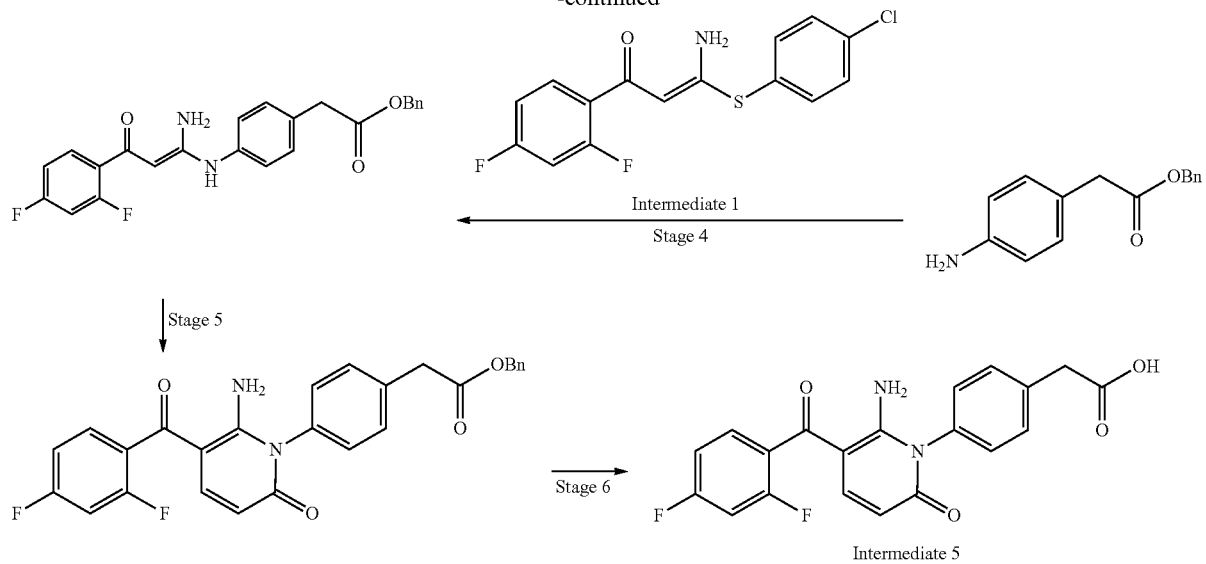

Stage 1—{4-[(tert-Butoxycarbonyl)amino] phenyl}acetic acid

To a solution of 3-(4-aminophenyl)acetic acid (5.00 g, 33 mmol) in aqueous 0.2N sodium hydroxide (40 ml) was added di-tert-butyl dicarbonate (7.22 g, 33 mmol) and the reaction mixture stirred at RT overnight. The reaction was acidified to pH 2 with 1M HCl and extracted with EtOAc (3×50 ml). The combined organic extracts were washed with brine (50 ml), dried (MgSO$_4$), filtered and concentrated under reduced pressure to leave a beige solid. Recrystallisation from ethanol/heptane afforded the title compound (5.70 g, 68% yield).

LC/MS: m/z 274 [M+Na]$^+$.

Stage 2—Benzyl {4-[(tert-butoxycarbonyl)amino] phenyl}acetate

To a solution of {4-[(tert-Butoxycarbonyl)amino] phenyl}acetic acid (5.70 g, 22.7 mmol) in DCM (60 ml) were added EDCl (4.78 g, 25 mmol), DMAP (277 mg, 2.3 mmol) and benzyl alcohol (4.7 ml, 45.4 mmol). The reaction mixture was stirred at RT over night then washed with 1M HCl (50 ml), sat. Na$_2$CO$_3$ (50 ml). The organic layer was separated from the aqueous and dried (MgSO$_4$) filtered and concentrated under reduced pressure to leave a pale brown oil. Purification by column chromatography (30% EtOAc in heptane) afforded the title compound as solid (7.75 g, 100% yield).

LC/MS: m/z 364 [M+Na]$^+$.

Stage 3—Benzyl (4-aminophenyl)acetate

To a solution of benzyl {4-[(tert-butoxycarbonyl)amino] phenyl}acetate (8.15 g, 23.8 mmol) in DCM (50 ml) was added TFA (25 ml). The reaction mixture was stirred at RT overnight then concentrated under reduced pressure to leave yellow oil. Trituration with Et$_2$O afforded a pale yellow solid. This was partitioned between EtOAc (100 ml) and sat. Na$_2$CO$_3$ (100 ml). The organic layer was separated, washed with brine (30 ml, dried (MgSO$_4$), filtered and concentrated under reduced pressure to leave a yellow oil (3.78 g, 69% yield)

LC/MS: m/z 242 [M+H]$^+$.

Stage 4—Benzyl (4-{[(1E)-1-amino-3-(2,4-difluorophenyl)-3-oxoprop-1-en-1-yl]amino}phenyl)acetate Benzyl (4-aminophenyl)acetate (3.78 g, 12.1 mmol) and 4-chlorophenyl 3-(2,4-difluorophenyl)-3-oxopropanimidothioate (Intermediate 1) (4.4 g, 12.1 mmol) were dissolved in acetic acid (45 ml) and the mixture stirred at 80° C. for 1 hour then concentrated under reduced pressure. The resulting yellow oil was triturated in Et$_2$O to afford a pale yellow solid. This solid was suspended in sat. NaHCO$_3$ (200 ml) and vigorously stirred at RT for 30 minutes. A yellow solid was collected by filtration thoroughly washed with water and dried under reduced pressure to give a yellow solid (5.13 g, 100%).

LC/MS: m/z 423 [M+H]$^+$.

Stage 5—Benzyl {4-[6-amino-5-(2,4-difluorobenzoyl)-2-oxopyridin-1(2H)-yl]phenyl}acetate To a solution of CDI (2.95 g, 18.2 mmol) in THF (100 ml), under N$_2$ at 0° C., was added dropwise propiolic acid (1.12 ml, 18.2 mmol). The mixture was warmed to room temperature and stirred for 1 hour. A solution of benzyl (4-{[(1E)-1-amino-3-(2,4-difluorophenyl)-3-oxoprop-1-en-1-yl] amino}phenyl)acetate (5.13 g, 12.1 mmol) in THF (50 ml) was added dropwise and the mixture heated at 80° C. overnight. The mixture was cooled to RT. A beige solid was collected by filtration and discarded (undesired by-product). The filtrated was concentrated under reduced pressure to leave a brown oil. Trituration with EtOAc afforded a brown sticky solid which was discarded too as contained only a small amount of desired product. The filtrate from trituration was concentrated in vacuo to afford a brown solid. Trituration with a small amount of MeOH and Et$_2$O afforded the title compound as a beige solid (1.05 g, 18% yield).

LC/MS: m/z 475 [M+H]$^+$.

Stage 6—{4-[6-amino-5-(2,4-difluorobenzoyl)-2-oxopyridin-1(2H)-yl]phenyl}acetic acid Benzyl {4-[6-amino-5-(2,4-difluorobenzoyl)-2-oxopyridin-1(2H)-yl]phenyl}acetate (1.05 g, 2.21 mmol) was dissolved in EtOAc (50 ml). The solution was degassed and flushed with nitrogen before adding Pd/C (200 mg). The resulting suspension was flushed with nitrogen (×3), with hydrogen then stirred at RT for 2 hours. The reaction mixture was filtered through a pad of celite, which was then thoroughly washed with EtOAc. The combined filtrated were concentrated under reduced pressure to leave an pale orange solid (0.65 g, 77%)

LC/MS: m/z 385 [M+H]$^+$. $^1$H NMR (300 MHz, DMSO-$d_6$) δ: 7.56-7.48 (3H, m), 7.41 (1H, td, J=2.5, 9.8 Hz), 7.32-7.20 (4H, m), 5.72 (1H, d, J=9.8 Hz), 3.70 (2H, s).

Intermediate 6: 3-{4-[6-amino-5-(2,4-difluorobenzoyl)-2-oxopyridin-1(2H)-yl]-3,5-difluorophenoxy}propanal

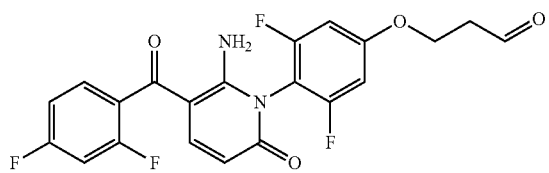 [SMILES: Nc1c(C(=O)c2ccc(F)cc2F)ccc(=O)n1-c1c(F)cc(OCCC=O)cc1F]

Intermediate 6 was synthesised using the route shown in Scheme 5 below

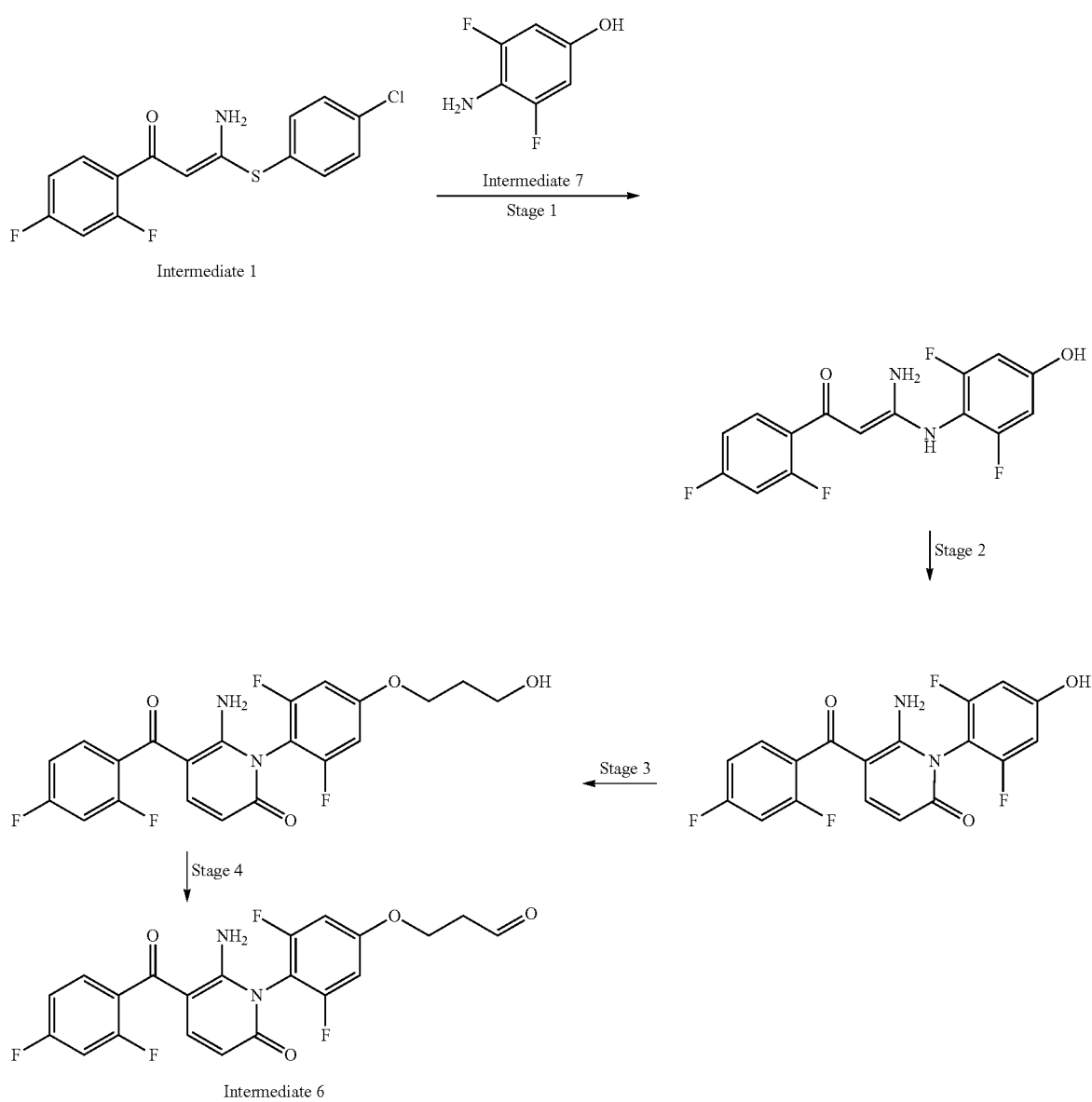

Stage 1—(2E)-3-amino-3-[(2,6-difluoro-4-hydroxyphenyl)amino]-1-(2,4 difluorophenyl)prop-2-en-1-one Stage 1 product was prepared in a similar manner to Stage 1 product of Intermediate 4 (Scheme 3)
LC/MS: m/z 327 [M+H]+.

Stage 2—6-amino-5-(2,4-difluorobenzoyl)-1-(2,6-difluoro-4-hydroxyphenyl)pyridin-2(1H)-one Stage 2 product was prepared in a similar manner to Stage 2 product of Intermediate 4 (Scheme 3)
LC/MS: m/z 379 [M+H]+.

Stage 3—6-amino-5-(2,4-difluorobenzoyl)-1-[2,6-difluoro-4-(3 hydroxypropoxy)phenyl]pyridin-2(1H)-one To a solution of 6-amino-5-(2,4-difluorobenzoyl)-1-(2,6-difluoro-4-hydroxyphenyl)pyridin-2(1H)-one (1 g, 2.6 mmol) in acetone (25 ml) was added 3-bromopropan-1-ol (0.26 ml, 2.9 mmol) followed by sodium iodide (0.8 g, 5.3 mmol) and potassium carbonate (1.46 g, 10.6 mmol). The reaction mixture was stirred at 70° C. under an atmosphere of nitrogen for 8 hours and then concentrated under reduced pressure. The residue was triturated with water and Et₂O. The resulting solid was filtered in vacuo to leave an off white solid (0.7 g, 61%).
LC/MS: m/z 437 [M+H]+.

Stage 4—3-{4-[6-amino-5-(2,4-difluorobenzoyl)-2-oxopyridin-1(2H)-yl]-3,5-difluorophenoxy}propanal To a solution of 6-amino-5-(2,4-difluorobenzoyl)-1-[2,6-difluoro-4-(3 hydroxypropoxy)phenyl]pyridin-2(1H)-one (0.25 g, 0.57 mmol) in DCM (10 ml) was added Dess Martin periodinane (0.29 g, 0.69 mmol) and the mixture stirred at RT overnight. The reaction was quenched with a 1:1 mixture of sat. NaHCO₃ (5 ml) and sodium thiosulfate (5 ml). The biphasic mixture was filtered to afford a pale yellow solid. This was washed with water and Et₂O to leave an off white solid (0.2 g, 82%)
LC/MS: m/z 435 [M+H]+.

Intermediate 7: Cyclopentyl 2-methylalaninate hydrochloride

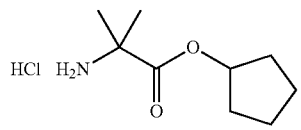

Intermediate 7 was synthesised using the route shown in Scheme 6 below.

Scheme 6

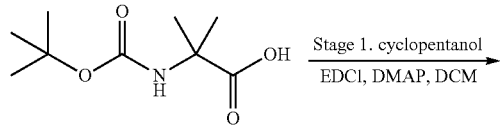

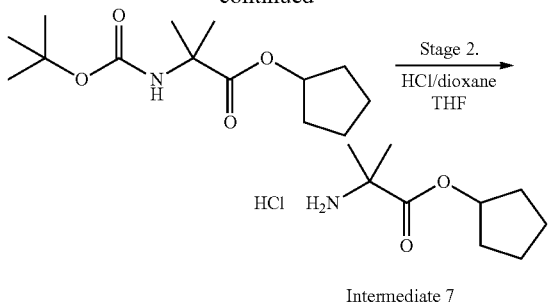

Intermediate 7

Stage 1—Cyclopentyl N-(tert-butoxycarbonyl)-2-methylalaninate

To a solution of N-(tert-butoxycarbonyl)-2-methylalanine (1.00 g, 4.92 mmol) in DCM (10 ml) at 0° C. was added cyclopentanol (0.83 ml, 9.84 mmol), EDCI (1.06 g, 5.42 mmol) and finally DMAP (60 mg, 0.49 mmol). The reaction mixture was warmed to RT and stirred for 18 hours. The DCM was removed in vacuo to give a clear oil. The crude residue was dissolved in EtOAc (100 ml) and washed with water, 1 M NaHCO₃ and brine. The organic phase was dried (MgSO₄) and concentrated in vacuo. The crude extract was purified by column chromatography (10% EtOAc in heptane) to yield the desired product as a clear oil (0.254 g, 20% yield).
¹H NMR (300 MHz, CDCl₃) δ: 5.25-5.17 (1H, m), 5.04 (1H, br s), 1.93-1.54 (8H, m), 1.49 (6H, s), 1.45 (9H, s).

Stage 2—Cyclopentyl 2-methylalaninate hydrochloride

Cyclopentyl N-(tert-butoxycarbonyl)-2-methylalaninate (0.254 g, 0.93 mmol) was dissolved in THF (5 ml) and treated with 4M HCl/dioxane (2 ml) and the reaction mixture was stirred at RT for 24 hours. The crude mixture was concentrated under reduced pressure and triturated with Et₂O to give a white precipitate. This was further washed with Et₂O to give the desired product as a white powder (0.16 g, 82% yield).
¹H NMR (300 MHz, DMSO-d₆) δ: 8.58 (3H, br s), 5.21-5.14 (1H, m), 1.93-1.78 (2H, m), 1.74-1.53 (6H, m), 1.45 (6H, s).

Intermediate 8: tert-Butyl 2-methylalaninate

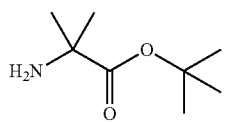

Intermediate 8 was synthesised using the route shown in Scheme 7 below.

Scheme 7

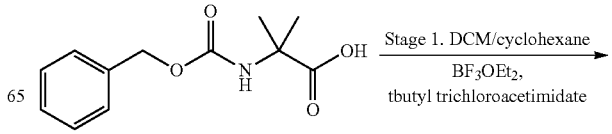

-continued

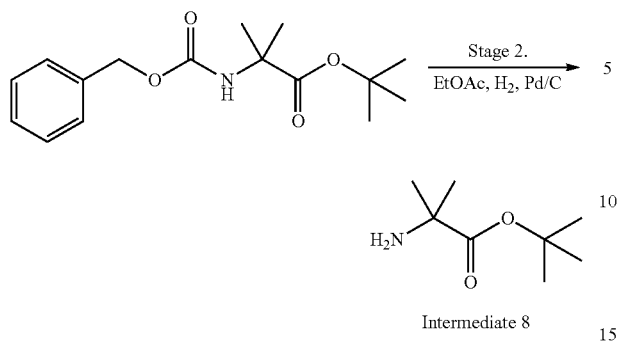

Intermediate 8

Stage 1—tert-Butyl N-[(benzyloxy)carbonyl]-2-methylalaninate

To a solution of N-[(benzyloxy)carbonyl]-2-methylalanine (1 g, 4.21 mmol) in DCM (10 ml anhydrous), cyclohexane (10 ml) at 0° C. under nitrogen was added boron trifluoride diethyl etherate (7.7 µl, catalytic). tert-Butyl 2,2,2-trichloroacetimidate (1.51 ml, 8.43 mmol) in cyclohexane (10 ml) was then added slowly over 30 minutes before allowing to warm to RT. Reaction was allowed to stir at RT for 16 hours. To the crude reaction mixture was added 190 mg of NaHCO$_3$ and the reaction filtered. The mother liquors were concentrated in vacuo. The crude extract was purified by column chromatography (10% EtOAc in heptane) to yield the desired product (0.863 g, 70% yield).

$^1$H NMR (300 MHz, CDCl$_3$) δ: 7.39-7.31 (5H, m), 5.46 (1H, br s), 5.10 (2H, s), 1.54 (6H, s), 1.45 (9H, s).

Stage 2—tert-butyl 2-methylalaninate

To a solution of tert-Butyl N-[(benzyloxy)carbonyl]-2-methylalaninate (0.863 mg, 2.90 mmol) in EtOAc (20 ml) was added 100 mg of Pd/C catalyst. The mixture was evacuated and stirred under an atmosphere of hydrogen for 18 hours, filtered (Celite), washed with EtOAc and concentrated in vacuo. The product was isolated as a yellow oil (0.45 mg, 96% yield) which contained traces of EtOAc. The product is believed to be volatile so caution is needed during evaporation in vacuo.

$^1$H NMR (300 MHz, CDCl$_3$) δ: 1.48 (9H, s), 1.32 (6H, s).

Intermediate 9: Cyclopentyl 1-aminocyclopentanecarboxylate

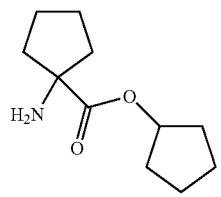 [SMILES: NC1(C(=O)OC2CCCC2)CCCC1]

Intermediate 9 was synthesised using the route shown in Scheme 8 below.

Scheme 8

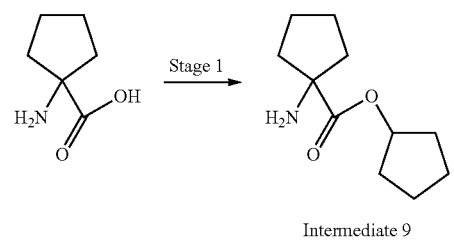

Intermediate 9

Stage 1—Cyclopentyl 1-aminocyclopentanecarboxylate

To a solution of 1-aminocyclopentanecarboxylic acid (2.58 g, 19.97 mmol) in cyclopentanol (20 ml), was added concentrated sulfuric acid (2.15 g, 21.97 mmol) and the mixture stirred overnight at 70° C. The reaction was allowed to cool to RT and the cyclopentanol removed under reduced pressure. The residue was dissolved in EtOAc (30 ml) and washed with sat. NaHCO$_3$ (30 ml) and water (3×20 ml) then dried (MgSO$_4$), filtered and concentrated in vacuo to leave a dark yellow oil. Purification by column chromatography (15% 1.2 M NH$_3$/MeOH in EtOAc) afforded the desired product (1.97 g, 50% yield).

$^1$H NMR (300 MHz, CDCl$_3$) δ: 5.21-5.17 (1H, m), 2.15-1.90 (2H, m), 1.85-1.57 (14H, m).

Intermediate 10: tert-Butyl 1-aminocyclopentanecarboxylate

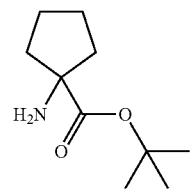

Intermediate 10 was synthesised using the route shown in Scheme 9 below.

Scheme 9

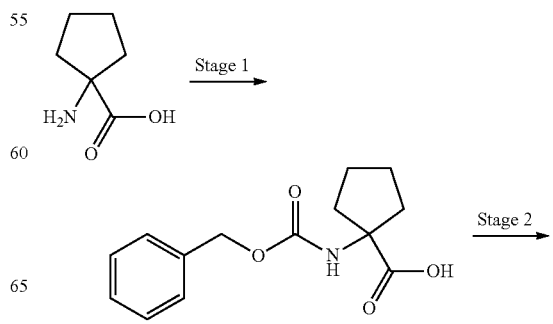

Intermediate 11: Cyclopentyl L-isovalinate

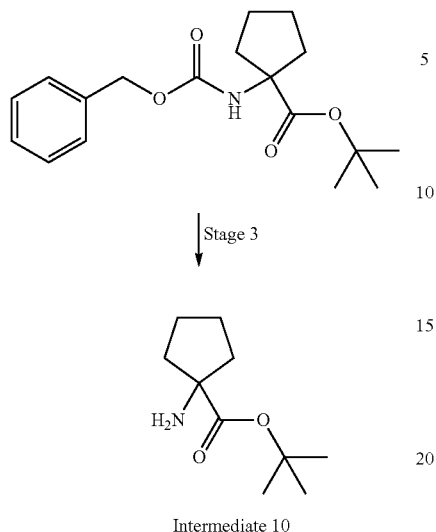

Intermediate 10

Stage 1—1-{[(benzyloxy)carbonyl]amino}cyclopentanecarboxylic acid

To a solution of 1-aminocyclopentanecarboxylic acid (3.0 g, 23.2 mmol) in 1:1 dioxane/water (60 ml), was slowly added $Na_2CO_3$ (12.3 g, 116 mmol) followed by benzyl chloroformate (3.6 ml, 25.5 mmol) and the mixture stirred overnight at RT. The reaction mixture was carefully acidified to pH 2 with 1 M HCl then extracted with EtOAc (3×30 ml). The combined organic extracts were washed with brine (30 ml), dried ($MgSO_4$), filtered and concentrated in vacuo to leave a pale yellow oil. LCMS and NMR showed the crude product to be a mixture of desired product and corresponding benzyl ester. The crude product was dissolved in 1:1 THF/water (60 ml) and treated with lithium hydroxide (2.67 g, 116 mmol). The mixture was stirred at RT over night then washed with $Et_2O$ (3×30 ml), acidified to pH 2 and extracted with EtOAc (3×30 ml). The combined organic extracts were washed with brine (30 ml), dried ($MgSO_4$), filtered and concentrated under reduced pressure to afford the title compound (4.76 g, 78%). LCMS: m/z 264 [M+H]$^+$.

Stage 2—tert-Butyl 1-{[(benzyloxy)carbonyl]amino}cyclopentanecarboxylate tert-Butyl 1-{[(benzyloxy)carbonyl]amino}cyclopentanecarboxylate was prepared in a similar fashion to Stage 1 (Scheme 7) of Intermediate 8.

LC/MS: m/z 320 [M+H]$^+$.

Stage 3—tert-Butyl 1-aminocyclopentanecarboxylate tert-Butyl 1-aminocyclopentanecarboxylate was prepared in a similar fashion to Stage 2 (Scheme 7) of Intermediate 8.

$^1$H NMR (300 MHz, CDCl$_3$) δ: 2.08-2.02 (2H, m), 1.87-1.72 (4H, m), 1.64-1.58 (2H, m), 1.47 (9H, s).

Intermediate 11: Cyclopentyl L-isovalinate

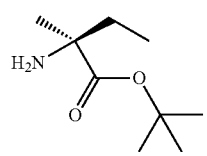

Intermediate 11 was synthesized following the one step process shown below.

To a solution of L-isovaline hydrochloride (2 g, 13 mmol) in cyclopentanol (20 ml) was added conc. sulfuric acid (0.76 ml, 14 mmol). Reaction was heated to 70° C. and stirred overnight. The reaction was cooled and evaporated under reduced pressure to give a yellow oil which was dissolved in 2M HCl (25 ml) and washed with $Et_2O$ (2×20 ml). The aqueous layer was then adjusted to pH 12 with 2M NaOH and extracted with EtOAc (3×20 ml). The combined organic extracts were dried ($MgSO_4$), filtered and concentrated under reduced pressure. Purification by column chromatography (5% MeOH in DCM) afforded the title compound as a colourless oil (0.4 g, 16%).

LC/MS: m/z 186 [M+H]$^+$.

Intermediate 12: tert-Butyl L-isovalinate

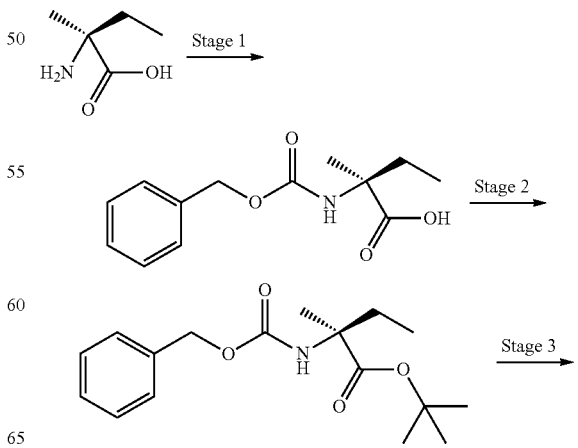

Intermediate 12 was synthesised using the route shown in Scheme 10 below.

Scheme 10

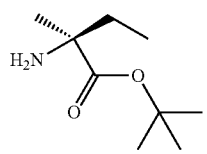

Intermediate 12

Stage 1—N-[(benzyloxy)carbonyl]-L-isovaline

To a solution of L-isovaline hydrochloride (2 g, 13 mmol) in 1:1 mixture of dioxane and water (40 ml) was slowly added Na$_2$CO$_3$ (6.9 g, 26 mmol) followed by benzoylchloroformate (3.7 ml, 65 mmol). The mixture was stirred at RT overnight. The reaction was carefully acidified to pH 2 with conc. HCl and extracted with EtOAc (3×30 ml). The combined organic extracts were washed with brine (30 ml), dried (MgSO$_4$), filtered and concentrated under reduced pressure to leave a pale yellow oil (2 g, 61%). LC/MS: m/z 252 [M+H]$^+$.

Stage 2—tert-butyl N-[(benzyloxy)carbonyl]-L-isovalinate

To a solution of N-[(benzyloxy)carbonyl]-L-isovaline (2 g, 8 mmol) in DCM (20 ml) and cyclohexane (20 ml) at 0° C. was added borontrifluoride diethyletherate (0.02 ml, 0.16 mmol). A solution of t-butyl-2,2,2-trichloroacetimidate (2.85 ml, 16 mmol) in cyclohexane (10 ml) was added dropwise over 15 mins and the mixture stirred at 0° C. for 15 mins. The reaction was allowed to warm to RT and stirred for 2.5 hours. Solid NaHCO$_3$ was added and the reaction mixture was filtered. The filtrated was concentrated under reduced pressure leave the crude product. Purification by column chromatography (10% EtOAc in heptane) afforded the title compound as a colourless oil (1.39 g, 57%). LC/MS: m/z 330 [M+Na]$^+$.

Stage 3—tert-butyl L-isovalinate

To a solution of tert-butyl N-[(benzyloxy)carbonyl]-L-isovalinate (1.39 g, 4.52 mmol) was dissolved in EtOAc (25 ml) under an atmosphere of nitrogen was added Pd/C (0.15 g). The suspension was flushed with nitrogen (×3) then with hydrogen and stirred under 1 atm of hydrogen at RT for 2 hours. The reaction mixture was filtered through a pad of celite and the filtrate was concentrated under reduced pressure to leave a colourless oil (0.8 g, 100%). LC/MS: m/z 174 [M+H]$^+$.

Intermediate 13: 2,3-dihydro-1H-inden-2-yl 2-methylalaninate

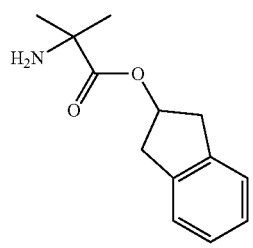 [SMILES: CC(C)(N)C(=O)OC1Cc2ccccc2C1]

Intermediate 13 was synthesised using the route shown in Scheme 11 below.

Scheme 11

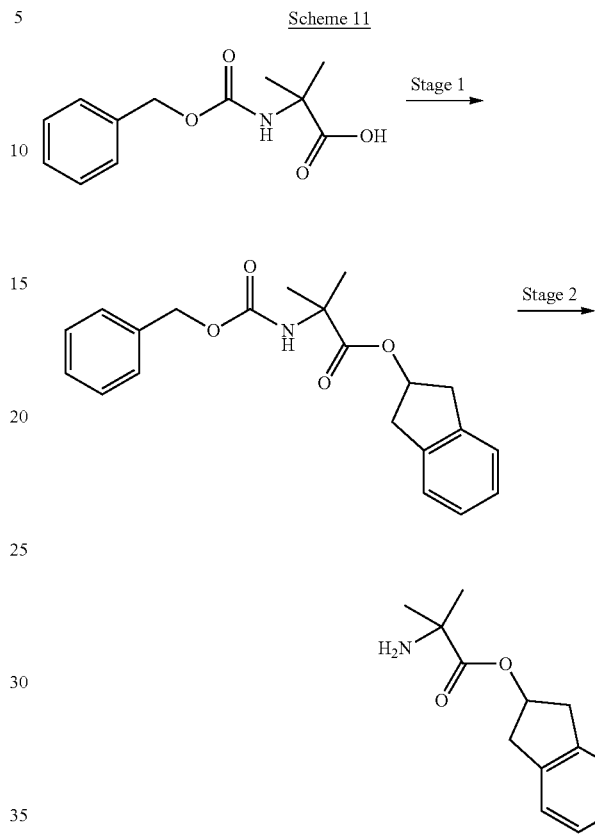

Stage 1—2,3-dihydro-1H-inden-2-yl N-[(benzyloxy)carbonyl]-2-methylalaninate

To a solution of N-[(benzyloxy)carbonyl]-2-methylalanine (2.00 g, 8.4 mmol) in DCM (10 ml) at 0° C. was added indanol (2.26 g, 16.9 mmol), EDCI (1.78 g, 9.3 mmol) and finally DMAP (103 mg, 0.8 mmol). The reaction mixture was warmed to RT and stirred for 18 hours. The reaction mixture was washed with 1M HCl (10 ml), sat. Na$_2$CO$_3$ (20 ml), dried (MgSO$_4$) filtered and concentrated in vacuo to leave a brown oil. The crude product was purified by column chromatography (20% EtOAc in heptane) to yield the desired product as a white solid (2.26 g, 76%). LC/MS: m/z 354 [M+H]$^+$.

Stage 2—2,3-dihydro-1H-inden-2-yl 2-methylalaninate

To a solution of 2,3-dihydro-1H-inden-2-yl N-[(benzyloxy)carbonyl]-2-methylalaninate (2.26 g, 6.39 mmol) was dissolved in EtOAc (30 ml) under an atmosphere of nitrogen was added Pd/C (0.2 g). The suspension was flushed with nitrogen (×3) then with hydrogen and stirred under 1 atm of hydrogen at RT overnight. The reaction mixture was filtered through a pad of celite and the filtrate was concentrated under reduced pressure to leave a pale yellow oil (1.35 g, 96%). LC/MS: m/z 220 [M+H]$^+$.

Intermediate 14: bicyclo[2.2.1]hept-2-yl 2-methylalaninate

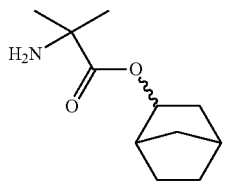

Intermediate 14 was synthesized following a similar method used in the preparation of Intermediate 13 using norborneol at Stage 1 of Scheme 11.
LC/MS: m/z 198 [M+H]+.

EXAMPLES

Example 1

Cyclopentyl N-(2-{4-[6-amino-5-(2,4-difluorobenzoyl)-2-oxopyridin-1(2H)-yl]phenyl}ethyl)-2-methylalaninate

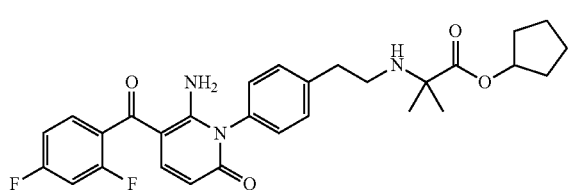 [SMILES: CC(C)(NCCc1ccc(-n2c(N)c(C(=O)c3ccc(F)cc3F)ccc2=O)cc1)C(=O)OC1CCCC1]

Example 1 was synthesised using Intermediate 2 and Intermediate 7 as described below.

To a solution of Intermediate 2 (189 mg, 0514 mmol) in anhydrous THF (4 ml) were added cyclopentyl 2-methylalaninate hydrochloride (Intermediate 7) (160 mg, 0.77 mmol, 1.5 eq) and NaBH(OAc)$_3$ (326 mg, 1.54 mmol, 3 eq). The mixture was stirred at room temperature for 16 hours, and then quenched with water (20 ml). The aqueous layer was extracted with EtOAc (3×20 ml), and the combined organic extracts washed with brine (40 ml), dried over MgSO$_4$, filtered and concentrated under reduced pressure. The residue was purified by preparative HPLC to provide the title compound (130 mg, 48% yield).

LC/MS: m/z 524 [M+H]+. $^1$H NMR (300 MHz, CDCl$_3$) δ: 10.43 (1H, br s), 7.51-7.34 (4H, m), 7.28-7.26 (2H, m), 7.04-6.90 (2H, m), 5.93 (1H, d, J=9.6 Hz), 5.20-5.10 (1H, m), 2.93-2.75 (4H, m), 1.95-1.55 (8H, m), 1.31 (6H, s).

Example 2

Cyclopentyl N-(2-{4-[6-amino-5-(2,4-difluorobenzoyl)-2-oxopyridin-1(2H)-yl]-3,5-difluorophenyl}ethyl)-2-methylalaninate

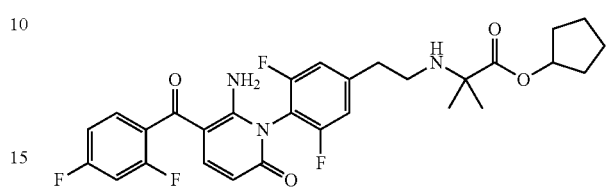

Example 2 was synthesised using Intermediate 4 and Intermediate 7 in a similar manner to Example 1.

LC/MS: m/z 560 [M+H]+. $^1$H NMR (300 MHz, CDCl3) δ: 7.48-7.39 (2H, m), 7.09-6.92 (4H, m), 5.92 (1H, d, J=9.6 Hz), 5.13 (1H, br s), 2.87-2.81 (4H, m), 2.05-1.89 (2H, m), 1.76-1.62 (6H, m), 1.30 (6H, s).

Example 3

Cyclopentyl N-({4-[6-amino-5-(2,4-difluorobenzoyl)-2-oxopyridin-1(2H)-yl]phenyl}acetyl)-2-methylalaninate

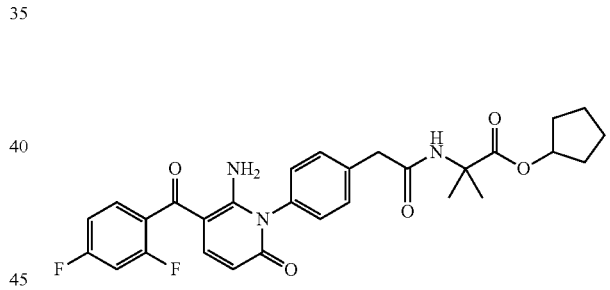

To a solution of {4-[6-amino-5-(2,4-difluorobenzoyl)-2-oxopyridin-1(2H)-yl]phenyl}acetic acid (Intermediate 5) (0.1 g, 0.26 mmol) in DCM/DMF (1:1, 6 ml) were added EDCI (0.055 g, 0.29 mmol), DMAP (0.003 g, 0.03 mmol) and triethylamine (40 µl, 0.29 mmol) followed by the addition of cyclopentyl 2-methylalaninate hydrochloride (Intermediate 7) (0.059 g, 0.29 mmol). The mixture was stirred at RT overnight. The reaction mixture was diluted with EtOAc (20 ml), washed with water (2×20 ml), brine (20 ml) then dried (MgSO$_4$), filtered and concentrated under reduced pressure to leave a yellow oil. Purification by column chromatography (100% EtOAc) afforded the title compound as a pale yellow solid (68 mg, 48%)

LC/MS: m/z 538 [M+H]+. $^1$H NMR (300 MHz, DMSO-d$_6$) δ: 8.48 (1H, s), 7.55-7.37 (4H, m), 7.29-7.20 (4H, m), 5.72 (1H, d, J=9.6 Hz), 5.03-4.99 (1H, m), 3.54 (2, s), 1.78-1.69 (2H, m), 1.63-1.47 (6H, m), 1.36 (6H, s).

Examples 4-10 were synthesised in a similar manner to Example 1.

Example 4

Cyclopentyl 1-[(2-{4-[6-amino-5-(2,4-difluorobenzoyl)-2-oxopyridin-1(2H)-yl]phenyl}ethyl)amino]cyclopentanecarboxylate

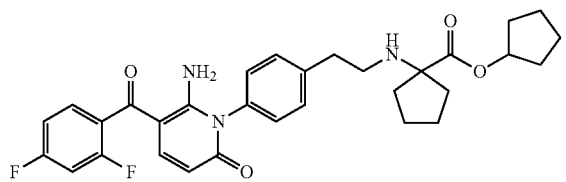 [SMILES: Nc1c(C(=O)c2ccc(F)cc2F)ccc(=O)n1-c1ccc(CCNC2(C(=O)OC3CCCC3)CCCC2)cc1]

From Intermediate 2 and Intermediate 9.

LC/MS: m/z 550 [M+H]⁺. ¹H NMR (300 MHz, DMSO-d6) δ: 7.55-7.34 (6H, m), 7.29-7.21 (2H, m), 5.72 (1H, d, J=9.8 Hz), 5.27-5.21 (1H, m), 3.31-3.20 (2H, m), 3.10-3.00 (2H, m), 2.22-2.12 (2H, m), 2.08-1.98 (2H, m), 1.90-1.58 (12H, m)

Example 5

Cyclopentyl N-(2-{4-[6-amino-5-(2,4-difluorobenzoyl)-2-oxopyridin-1(2H)-yl]phenyl}ethyl)-L-isovalinate

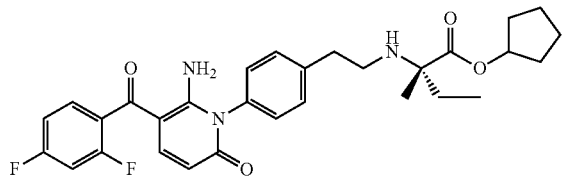 [SMILES: CC[C@](C)(NCCc1ccc(-n2c(N)c(C(=O)c3ccc(F)cc3F)ccc2=O)cc1)C(=O)OC1CCCC1]

From Intermediate 2 and Intermediate 11.

LC/MS: m/z 538 [M+H]⁺. ¹H NMR (300 MHz, DMSO-d₆) δ: 10.09 (1H, br s), 7.55-7.38 (4H, m), 7.27-7.21 (4H, m), 6.88 (1H, br s), 5.71 (1H, d, J=9.8 Hz), 5.09 (1H, br s), 2.77-2.63 (4H, m), 1.97 (1H, br s), 1.83-1.76 (2H, m), 1.68-1.55 (8H, m), 1.16 (3H, s), 0.79 (3H, t, J=7.3 Hz).

Example 6 tert-butyl N-(2-{4-[6-amino-5-(2,4-difluorobenzoyl)-2-oxopyridin-1(2H)-yl]phenyl}ethyl)-L-isovalinate

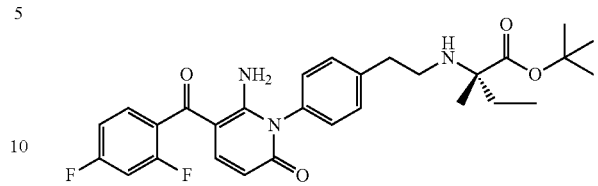

From Intermediate 2 and Intermediate 12.

LC/MS m/z 526 [M+H]⁺: 1H NMR (300 MHz, CD₃OD) δ: 7.54-7.42 (4H, m), 7.30-7.26 (2H, m), 7.15-7.08 (2H, m), 5.82 (1H, d, J=9.8 Hz), 2.95-2.84 (3H, m), 2.79-2.68 (1H, m), 1.71-1.59 (2H, m), 1.48 (9H, s), 1.26 (3H, s), 0.90-0.83 (3H, m).

Example 7

2,3-dihydro-1H-inden-2-yl N-(2-{4-[6-amino-5-(2,4-difluorobenzoyl)-2-oxopyridin-1(2H)-yl]phenyl}ethyl)-2-methylalaninate

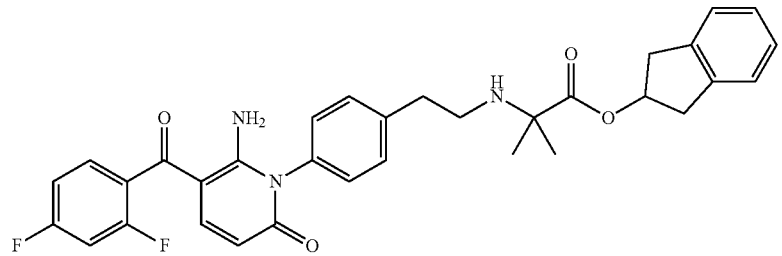 [SMILES: CC(C)(NCCc1ccc(-n2c(N)c(C(=O)c3ccc(F)cc3F)ccc2=O)cc1)C(=O)OC1Cc2ccccc2C1]

From Intermediate 2 and Intermediate 13.

LC/MS: m/z 572 [M+H]⁺ ¹H NMR (300 MHz, CDCl₃) 7.48-7.35 (4H, m), 7.27-7.20 (6H, m), 7.02 (1H, td, J=2.3, 7.9 Hz), 6.94 (1H, td, J=2.3, 9.1 Hz), 5.94 (1H, d, J=9.6 Hz), 5.56-5.50 (1H, m), 3.38 (2H, dd, J=6.4, 17.0 Hz), 3.01 (2H, dd, J=2.8, 17.0 Hz), 2.82-2.78 (2H, m), 1.30 (6H, s).

Example 8 bicyclo[2.2.1]hept-2-yl N-(2-{4-[6-amino-5-(2,4-difluorobenzoyl)-2-oxopyridin-1(2H)-yl]phenyl}ethyl)-2-methylalaninate

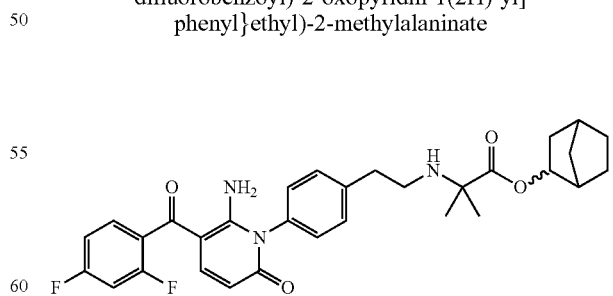

From Intermediate 2 and Intermediate 14.

LC/MS: m/z 499 [M+H]⁺ ¹H NMR (300 MHz, CDCl₃) 11.12 (1H, s), 7.52 (1H, s), 7.37-7.43 (1H, m), 7.28-7.32 (1H, m), 7.18-7.24 (1H, m), 7.07 (1H, s), 5.44 (2H, s), 4.64-4.70 (1H, m), 3.77-3.86 (1H, m), 3.60-3.67 (1H, m), 3.27 (1H, t,

J=7.2 Hz), 2.31 (2H, d, J=3.8 Hz), 1.69-1.90 (2H, m), 1.37-1.58 (4H, m), 1.08-1.23 (2H, m), 0.84-0.97 (6H, m).

Example 9

Cyclopentyl N-(3-{4-[6-amino-5-(2,4-difluorobenzoyl)-2-oxopyridin-1(2H)-yl]-3,5-difluorophenoxy}propyl)-2-methylalaninate

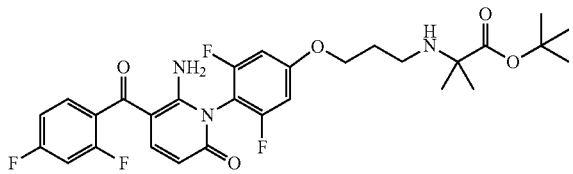 [SMILES: CC(C)(C)OC(=O)C(C)(C)NCCCOc1cc(F)c(-n2c(N)c(C(=O)c3ccc(F)cc3F)ccc2=O)c(F)c1]

From Intermediate 6 and Intermediate 7.
LC/MS m/z 590 [M+H]⁺: ¹H NMR (300 MHz, CDCl₃) 7.48-7.38 (2H, m), 7.02 (1H, td, J=2.1, 8.1 Hz), 6.94 (1H, td, J=2.5, 9.4 Hz), 6.74 (2H, d, J=9.4 Hz), 5.92 (2H, d, J=9.8 Hz), 5.23-5.19 (1H, m), 4.12 (2H, t, J=6.0 Hz), 2.69 (2H, t, J=6.8 Hz), 2.03-1.95 (2H, m), 1.92-1.84 (2H, m), 1.75-1.60 (6H, m), 1.31 (6H, s).

Example 10 tert-butyl N-(3-{4-[6-amino-5-(2,4-difluorobenzoyl)-2-oxopyridin-1(2H)-yl]-3,5-difluorophenoxy}propyl)-2-methylalaninate

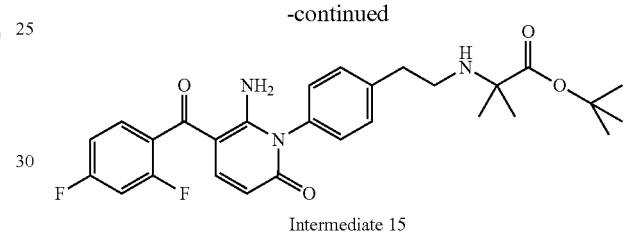

From Intermediate 6 and Intermediate 8.
LC/MS: m/z 578 [M+H]⁺¹H NMR (300 MHz, CDCl₃) 7.36-7.26 (2H, m), 6.93 (1H, td, J=2.1, 7.7 Hz), 6.86 (1H, td, J=2.3, 9.4 Hz), 6.64 (2H, d, J=9.2 Hz), 5.83 (1H, d, J=9.8 Hz), 4.03 (2H, t, J=6.0 Hz), 2.61 (2H, t, J=6.9 Hz), 1.95-1.86 (2H, m), 1.40 (9H, s), 1.20 (6H, s).

Example 11

N-(2-{4-[6-amino-5-(2,4-difluorobenzoyl)-2-oxopyridin-1(2H)yl]phenyl}ethyl)-2-methylalanine

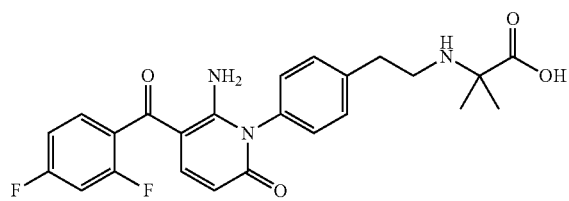 [SMILES: CC(C)(NCCc1ccc(-n2c(N)c(C(=O)c3ccc(F)cc3F)ccc2=O)cc1)C(=O)O]

Example 11 was synthesised using Intermediate 2 and Intermediate 8 as described in Scheme 12 below.

Scheme 12

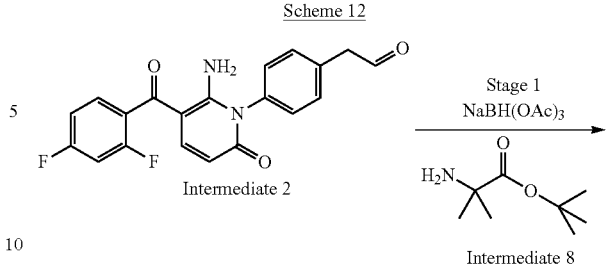

-continued

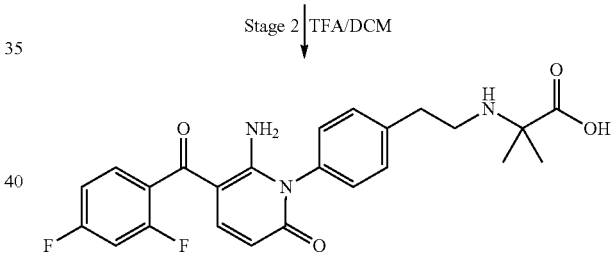

Stage 2 | TFA/DCM

Stage 1—tert-Butyl N-(2-{4-[6-amino-5-(2,4-difluorobenzoyl)-2-oxopyridin-1(2H)-yl]phenyl}ethyl)-2-methylalaninate To a solution of Intermediate 2 (180 mg, 0.489 mmol) in THF (3 ml) was added tert-butyl 2-methylalaninate (Intermediate 8) (117 mg, 0.73 mmol), stirred for 30 minutes, and then NaBH(OAc)₃ (310 mg, 1.467 mmol). The reaction was stirred for 24 hours, diluted with EtOAc and the organics washed with sat NaHCO₃, brine, dried (MgSO₄) and concentrated in vacuo. The residue was purified by preparative HPLC to provide the title compound (Intermediate 15) (120 mg, 48% yield).
LC/MS: m/z 512 [M+H]⁺. ¹H NMR (300 MHz, CDCl₃) δ: 10.41 (1H, br s), 7.51-7.34 (4H, m), 7.28-7.26 (2H, m), 7.05-6.90 (2H, m), 5.93 (1H, d, J=9.9 Hz), 5.15 (1H, br s), 2.93-2.78 (4H, m), 1.46 (9H, s), 1.29 (6H, s).

Stage 2—N-(2-{4-[6-amino-5-(2,4-difluorobenzoyl)-2-oxopyridin-1(2H)-yl]phenyl}ethyl)-2-methylalanine To a solution of Intermediate 15 (100 mg, 0.19 mmol) in DCM (3 ml) was added trifluoroacetic acid (3 ml). The mixture was stirred at room temperature for 16 hours and concentrated under reduced pressure. The residue was triturated with Et$_2$O, collected by filtration and dried under reduced pressure to afford the title compound as an off-white solid (50 mg, 56% yield).

LC/MS: m/z 456 [M+H]$^+$. $^1$H NMR (300 MHz, DMSO-d$_6$) δ: 10.05 (1H, br s), 7.60-7.15 (9H, m), 6.95 (1H, br s), 5.72 (1H, d, J=9.6 Hz), 3.15-2.95 (4H, m), 1.33 (6H, br s).

Example 12

N-(2-{4-[6-amino-5-(2,4-difluorobenzoyl)-2-oxopyridin-1(2H)-yl]-3,5-difluorophenyl}ethyl)-2-methylalanine

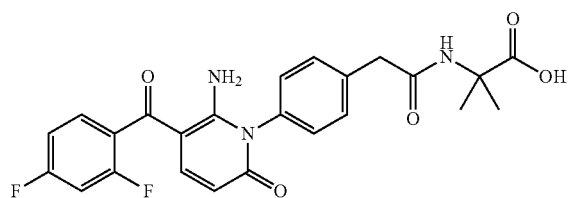 [SMILES: CC(C)(NC(=O)Cc1ccc(-n2c(N)c(C(=O)c3ccc(F)cc3F)ccc2=O)cc1)C(=O)O]

Example 12 was synthesised using Intermediate 4 and Intermediate 8 following the same synthetic route as Example 11 (Scheme 12).

LC/MS: m/z 492 [M+H]$^+$. $^1$H NMR (300 MHz, DMSO-d$_6$) δ: 7.62-7.54 (1H, m), 7.47-7.35 (4H, m), 7.27-7.21 (1H, m), 5.75 (1H, d, J=9.8 Hz), 3.44-3.07 (4H, m), 1.52 (6H, s).

Example 13

N-({4-[6-amino-5-(2,4-difluorobenzo-2-oxopyridin-1(2H)-yl]phenyl}acetyl)-2-methylalanine

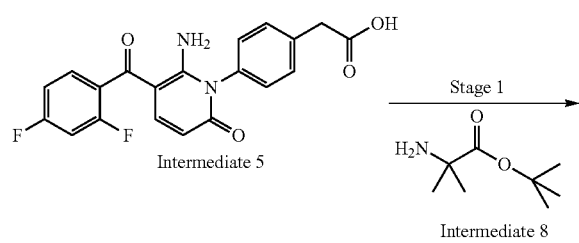

Example 13 was synthesized using Intermediate 5 and Intermediate 8 as described in Scheme 13 below.

Scheme 13

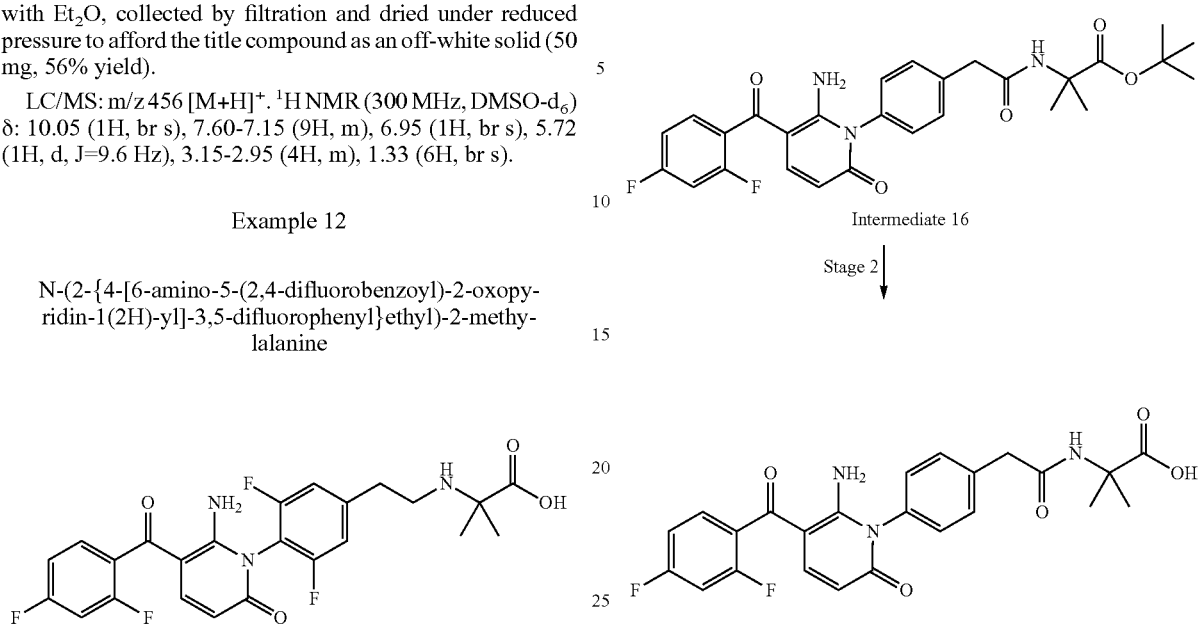

Stage 1—tert-Butyl N-({4-[6-amino-5-(2,4-difluorobenzoyl)-2-oxopyridin-1(2H)-yl]phenyl}acetyl)-2-methylalaninate (Intermediate 16)

To a solution of {4-[6-amino-5-(2,4-difluorobenzoyl)-2-oxopyridin-1(2H)-yl]phenyl}acetic acid (Intermediate 5) (0.13 g, 0.34 mmol) in DCM/DMF (1:1, 6 ml) were added EDCI (0.07 g, 0.36 mmol), DMAP (0.004 g, 0.03 mmol) followed by the addition of tert-butyl 2-methylalaninate (Intermediate 8) (0.057 g, 0.36 mmol). The mixture was stirred at RT for overnight. The reaction mixture was diluted with EtOAc (20 ml), washed with water (2×20 ml), brine (20 ml), dried (MgSO$_4$), filtered and concentrated under reduced pressure to leave a yellow oil. Purification by column chromatography (100% EtOAc) afforded the title compound as an off-white solid (78 mg, 44% yield).

LCMS: m/z 526 [M+H]$^+$. $^1$H NMR (300 MHz, CDCl3) δ: 7.57 (2H, d, J=8.4 Hz), 7.47-7.32 (4H, m), 7.02 (1H, t, J=8.3 Hz), 6.94 (1H, td, J=2.4, 9.3 Hz), 6.37 (1H, br.s), 5.93 (1H, d, J=9.9 Hz), 3.64 (2H, s), 1.58 (6H, s), 1.47 (9H, s).

Stage 2—N-({4-[6-amino-5-(2,4-difluorobenzoyl)-2-oxopyridin-1(2H)-yl]phenyl}acetyl)-2-methylalanine To a solution of Intermediate 16 (0.05 g, 0.095 mmol) in DCM (2 ml) was added TFA (1 ml). The reaction mixture was stirred at RT for 5 hours and then concentrated under reduced pressure to leave a yellow oil. Trituration with Et$_2$O afforded the title compound as an off-white solid (42 mg, 94%).

LCMS: m/z 470 [M+H]$^+$. $^1$H NMR (300 MHz, DMSO-d$_6$) δ: 12.19 (1H, s), 8.38 (1H, s), 7.55-7.37 (4H, m), 7.29-7.21 (4H, m), 5.71 (1H, d, J=9.6 Hz), 3.55 (2H, s), 1.38 (6H, s).

Example 14

N-(2-{4-[6-amino-5-(2,4-difluorobenzoyl)-2-oxopyridin-1(2H)-yl]phenyl}ethyl)-L-isovaline

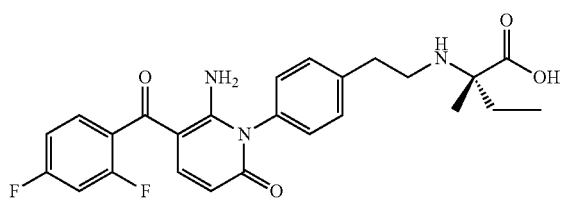 [SMILES: CC[C@](C)(NCCc1ccc(-n2c(N)c(C(=O)c3ccc(F)cc3F)ccc2=O)cc1)C(=O)O]

Example 14 was synthesized from Example 6 following a similar synthetic route described in Scheme 12.

Example 15

1-[(2-{4-[6-amino-5-(2,4-difluorobenzoyl)-2-oxopyridin-1(2H)-yl]phenyl}ethyl)amino]cyclopentanecarboxylic acid

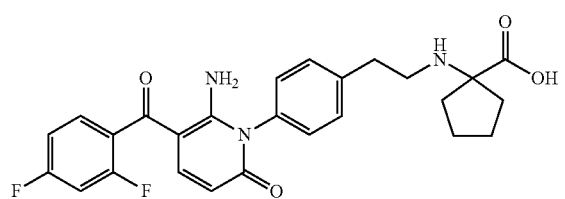 [SMILES: Nc1c(C(=O)c2ccc(F)cc2F)ccc(=O)n1-c1ccc(CCNC2(C(=O)O)CCCC2)cc1]

Example 15 was synthesized using Intermediate 2 and Intermediate 10 following a similar synthetic route described in Scheme 12.

LCMS: m/z 482 [M+H]$^+$. $^1$H NMR (300 MHz, DMSO-d$_6$) δ: 7.52-7.37 (4H, m), 7.31-7.20 (4H, m), 5.71 (1H, d, J=10.0 Hz), 3.08-2.93 (4H, m), 2.10-1.99 (2H, m), 1.78-1.68 (6H, m).

Example 16

N-(3-{4-[6-amino-5-(2,4-difluorobenzoyl)-2-oxopyridin-1(2H)-yl]-3,5-difluorophenoxy}propyl)-2-methylalanine

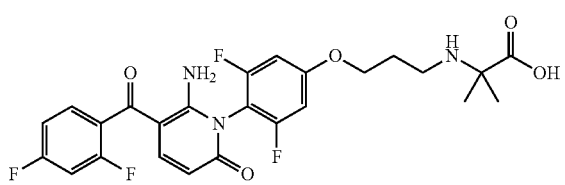 [SMILES: CC(C)(NCCCOc1cc(F)c(-n2c(N)c(C(=O)c3ccc(F)cc3F)ccc2=O)c(F)c1)C(=O)O]

Example 16 was synthesized from Example 10 following a similar synthetic route described in Scheme 12.

LC/MS: m/z 522 [M+H]$^+$. $^1$H NMR (300 MHz, CD$_3$OD) 7.56-7.49 (2H, m), 7.17-7.11 (2H, m), 6.95 (2H, d, J=10.1 Hz), 5.82 (1H, d, J=9.8 Hz), 4.25 (2H, t, J=5.7 Hz), 3.26-3.21 (2H, m), 2.30-2.21 (2H, m), 1.58 (6H, s).

Measurement of Biological Activities
p38 MAP Kinase Activity

The ability of compounds to inhibit p38 MAP a Kinase activity was measured in an assay performed by Upstate (Dundee UK). In a final reaction volume of 25 µL, p38 MAP Kinase a (5-10 mU) is incubated with 25 mM Tris pH 7.5, 0.002 mMEGTA, 0.33 mg/mL myelin basic protein, 10 mM MgAcetate and [g-33p-ATP] (specific activity approx. 500 cpm/pmol, concentration as required). The reaction is initiated by the addition of the MgATP mix. After incubation for 40 minutes at room temperature, the reaction is stopped by the addition of 5 µL of a 3% phosphoric acid solution. 10 µL of the reaction is then spotted onto a P30 filtermat and washed three times for 5 minutes in 75 mM phosphoric acid and once in methanol prior to drying and scintillation counting.

Duplicate data points are generated from a 1/3 log dilution series of a stock solution in DMSO. Nine dilutions steps are made from a top concentration of 10 µM and a 'no compound' blank is included. The standard radiometric filter-binding assay is performed at an ATP concentration at, or close to, the Km. Data from scintillation counts are collected and subjected to free-fit analysis by Prism software. From the curve generated, the concentration giving 50% inhibition is determined and reported.

p38 MAP Kinase Cellular Assay: Inhibition of Phosphorylation of MAPKAP-2

U937 or HUT78 cells were plated in RPMI 1640, and were incubated at 37° C., 5% CO$_2$ for 18 hours. 10 mM stocks of compounds were diluted media/0.1% DMSO to give a log or semi-log dilution series. The wells for 'no treatment' and 'anisomycin' were treated with 0.1% DMSO only. The cells were incubated at 37° C., 5% CO$_2$ for a further 4 hours. Anisomycin was added to all wells except 'no treatment' at a final concentration of 10 µM. The cells were incubated at 37° C., 5% CO$_2$ for 30 minutes before harvest. Plates were stood on ice whilst harvesting, and all following steps were carried out at 4° C. The cells were pelleted at 1000 rpm for 10 minutes at 4° C., the media aspirated, and the pellet washed with cold PBS. The pellets were lysed in 120 µl of SDS lysis buffer (62.5 mM Tris, pH 6.8, 2% SDS, 10% glycerol, 50 mM DTT, with protease inhibitors and phosphatase inhibitors added according to the manufacturer's recommendations). After 30 minutes on ice, the samples were sonicated for 5 seconds before centrifugation at 13,000 rpm 4° C. for 10 minutes to remove cell debris. 10 µl of the resulting gel samples were loaded per lane on NOVEX 4-12% Bis-Tris MOPS gels. Membranes from western transfer of gels were blotted with anti-phospho MAPKAP2, anti-phospho HSP27 and anti GAPDH according to the manufacturer's instructions. Signal was visualised using HRP-linked anti-rabbit or anti-mouse antibodies, ECL reagent and ECL film. IC$_{50}$ values for the various compounds were visualised from the resulting photographic images, using both band-shift and signal intensity.

LPS-Stimulation of THP-1 Cells

THP-1 cells were plated in 100 µl at a density of 4×10$^4$ cells/well in V-bottomed 96 well tissue culture treated plates and incubated at 37° C. in 5% CO$_2$ for 16 hours. 2 hours after the addition of the inhibitor in 100 µl of tissue culture media, the cells were stimulated with LPS (*E. coli* strain 005:B5, Sigma) at a final concentration of 1 µg/ml and incubated at 37° C. in 5% CO$_2$ for 6 hours. TNF-α levels were measured from cell-free supernatants by sandwich ELISA (R&D Systems #QTA00B).

LPS-Stimulation of Human Whole Blood

Whole blood was taken by venous puncture using heparinised vacutainers (Becton Dickinson) and diluted in an equal volume of RPMI1640 tissue culture media (Sigma). 100 µl was plated in V-bottomed 96 well tissue culture treated plates. 2 hours after the addition of the inhibitor in 100 μl of RPMI1640 media, the blood was stimulated with LPS (*E coli* strain 005:B5, Sigma) at a final concentration of 100 ng/ml and incubated at 37° C. in 5% $CO_2$ for 6 hours. TNF-α levels were measured from cell-free supernatants by sandwich ELISA (R&D Systems #QTA00B).

$IC_{50}$ values were allocated to one of three ranges as follows:
Range A: IC50<100 nM
Range B: 100 nM<IC50<1000 nM
Range C: $IC_{50>1000}$ nM

Results Table

| Example | Inhibitor activity versus p38 MAPKa | Inhibitor activity versus THP-1 TNFα release | Inhibitor activity versus human whole blood TNFα release |
|---|---|---|---|
| 1 | A | A | B |
| 2 | A | A | A |
| 3 | A | B | C |
| 4 | A | A | C |
| 5 | B | A | C |
| 6 | B | B | NT |
| 7 | B | A | C |
| 8 | A | A | C |
| 9 | A | A | B |
| 10 | A | A | C |
| 11 | A | NR | NR |
| 12 | A | NR | NR |
| 13 | B | NR | NR |
| 14 | A | NR | NR |
| 15 | B | NR | NR |
| 16 | A | NR | NR |

"NT" indicates the compound has not yet been tested in the assay in question.
"NR" indicates "Not Relevant". Examples 11-16 are the resultant carboxylic acid analogues of the amino acid esters that are cleaved inside cells. When these carboxylic acids are contacted with the cells, they do not penetrate into the cells and hence do not inhibit TNF-α in this assay.

Broken Cell Carboxylesterase Assay

Any given compound of the present invention wherein $R_1$ is an ester group may be tested to determine whether it meets the requirement that it be hydrolysed by intracellular esterases, by testing in the following assay.

Preparation of Cell Extract

U937 or Hut78 tumour cells (~$10^9$) were washed in 4 volumes of Dulbeccos PBS (~1 liter) and pelleted at 525 g for 10 min at 4° C. This was repeated twice and the final cell pellet was resuspended in 35 ml of cold homogenising buffer (Trizma 10 mM, NaCl 130 mM, $CaCl_2$ 0.5 mM pH 7.0 at 25° C.). Homogenates were prepared by nitrogen cavitation (700 psi for 50 min at 4° C.). The homogenate was kept on ice and supplemented with a cocktail of inhibitors at final concentrations of:
Leupeptin 1 μM
Aprotinin 0.1 μM
E64 8 μM
Pepstatin 1.5 μM
Bestatin 162 μM
Chymostatin 33 μM After clarification of the cell homogenate by centrifugation at 525 g for 10 min, the resulting supernatant was used as a source of esterase activity and was stored at −80° C. until required.

Measurement of Ester Cleavage

Hydrolysis of esters to the corresponding carboxylic acids can be measured using the cell extract, prepared as above. To this effect cell extract (~30 μg/total assay volume of 0.5 ml) was incubated at 37° C. in a Tris-HCl 25 mM, 125 mM NaCl buffer, pH 7.5 at 25° C. At zero time the ester (substrate) was then added at a final concentration of 2.5 μM and the samples were incubated at 37° C. for the appropriate time (usually 0 or 80 mins). Reactions were stopped by the addition of 3× volumes of acetonitrile. For zero time samples the acetonitrile was added prior to the ester compound. After centrifugation at 12000 g for 5 mins, samples were analysed for the ester and its corresponding carboxylic acid at room temperature by LCMS (Sciex API 3000, HP1100 binary pump, CTC PAL). Chromatography was based on a MeCN (75×2.1 mm) column and a mobile phase of 5-95% acetonitrile in water/0.1% formic acid.

Rates of hydrolysis are expressed in pg/mL/min.

Table 1 presents data showing that several amino acid ester motifs, conjugated to various intracellular enzyme inhibitors by several different linker chemistries are all hydrolysed by intracellular carboxyesterases to the corresponding acid.

TABLE 1

| Structure of amino acid ester conjugate | R | Linker | Hydrolysis Rate Range U937 Cells (pg/mL/min) | Preparation of amino ester conjugate |
|---|---|---|---|---|
| R-Linker—[6-methoxy-7-substituted quinoline linked via O-phenyl-NHC(O)Ph] | cyclopentyl ester of alanine (H2N-CH(R)-C(O)O-cyclopentyl) | —CH2CH2O— | 100-1000 | WO2006117552 |

TABLE 1-continued
| Structure of amino acid ester conjugate | R | Linker | Hydrolysis Rate Range U937 Cells (pg/mL/min) | Preparation of amino ester conjugate |
|---|---|---|---|---|
| 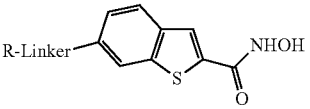 | 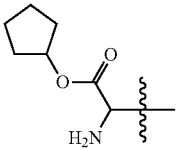 | —(CH₂)₃O—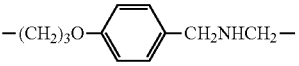—CH₂NHCH₂— | 1000-50000 | WO2006117548 |
| 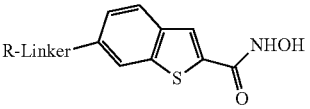 | 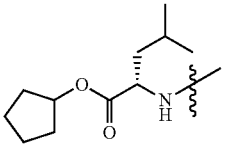 [SMILES: *N[C@@H](CC(C)C)C(=O)OC1CCCC1] | —CH₂—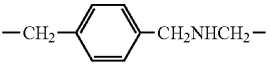—CH₂NHCH₂— | >50000 | WO2006117549 |
| 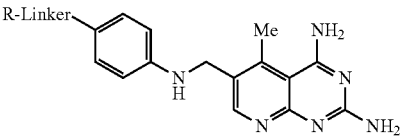 | 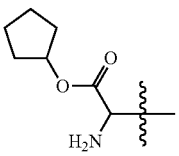 | —CH2CH2O— | >50000 | WO2006117567 |
|  | 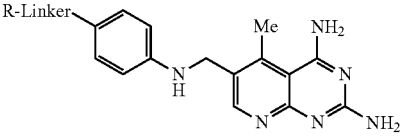 | —CH2CH2O— | 1000-50000 | WO2006117567 |
| 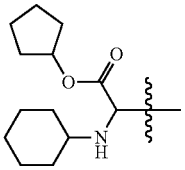 [SMILES: *C(NC1CCCCC1)C(=O)OC1CCCC1] | 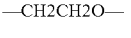 | —CH2— | 1000-50000 | WO2006117567 |
| 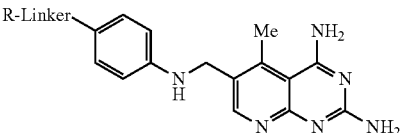 | 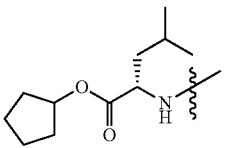 [SMILES: *N[C@@H](CC(C)C)C(=O)OC1CCCC1] | —CO— | >50000 | WO2006117567 |
|  | 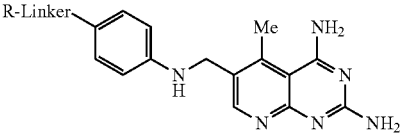 | —CH₂—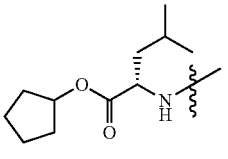 [SMILES: *N[C@@H](CC(C)C)C(=O)OC1CCCC1]—CH₂NHCH₂— | >50000 | WO2006117549 |
|  | 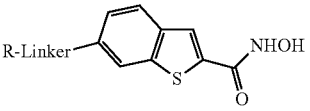 | —CH₂—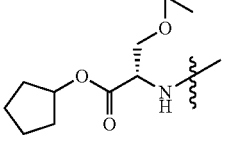—CH₂NHCH₂— | >50000 | WO2006117549 |

Table 2 shows that example 1 with the esterase motif attached is 30 times more potent in cells than the parent compound lacking the esterase motif even though the activities against the isolated enzyme are the same. The acid formed by cleavage of the ester in example 1 accumulates in U937 cells.

TABLE 2

| Compound | Inhibition of P38 (IC50, nM) | Inhibition of phosphorylation of MAPKAP-2 in U937 cells (IC50, nM) | Ratio cell IC50s to enzyme IC50 | Cell accumulation of the acid in U937 cells at 6 hours (ng/ml) |
|---|---|---|---|---|
| 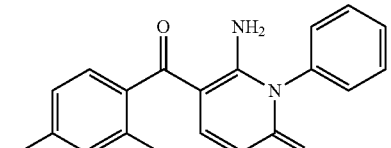<br>Compound I (parent) | 50 | 300 | 6 | NA |
| 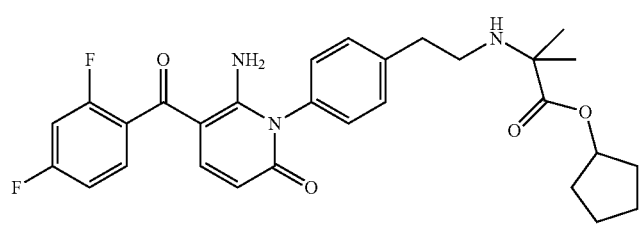<br>Example 1 | Ester 50 | Acid 50 | 10 | 0.2 | 987 |

Table 3 shows that the parent, compound I, is equipotent in monocytic and non-monocytic cell lines whereas example 1, is 100 times more potent in the monocytic cell line. Example 1 only accumulates in the monocytic cell line showing that the cell selectivity is achieved by the attachment of an esterase motif that is only cleaved in the monocytic cell line. It also shows that increased potency in the cells correlates with accumulation of the acid in the cells.

TABLE 3

| Compound | Inhibition of phosphorylation of MAPKAP-2 in U937 cells (IC50, nM) (monocyte cell line) | Inhibition of phosphorylation of MAPKAP-2 in HUT 78 cells (IC50, nM) (non-monocytic cell line) | Ratio IC50s in HUT 78 to U937 cells | Accumulation of the acid in U937 cells (ng/ml) | Accumulation of the acid in HUT 78 cells (ng/ml) |
|---|---|---|---|---|---|
| Parent Compound I | 300 | 450 | 1.5 | NA | NA |
| Example 1 | 10 | 1000 | 100 | 987 | 3 |

The invention claimed is:

1. A compound of formula (I), or a pharmaceutically acceptable salt thereof:

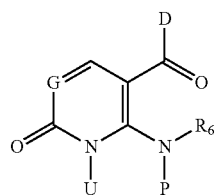

(I)

wherein:

G is —N= or —CH=

D is an optionally substituted divalent mono- or bi-cyclic aryl or heteroaryl radical having 5-13 ring members;

$R_6$ is hydrogen or optionally substituted $C_1$-$C_3$ alkyl;

P represents hydrogen and U represents a radical of formula (IA); or U represents hydrogen and P represents a radical of formula (IA);

-A-(CH$_2$)$_z$—X$^1$-L$^1$-Y—NH—CR$_1$R$_2$R$_3$    (IA)

wherein

A represents an optionally substituted divalent mono- or bicyclic carbocyclic or heterocyclic radical having 5-13 ring members;

z is 0 or 1;

Y is a bond, —C(=O)—, —S(=O)$_2$—, —C(=O)NR$_7$, —C(=S)—NR$_7$, —C(=NH)NR$_7$ or —S(=O)$_2$NR$_3$— wherein R$_7$ is hydrogen or optionally substituted C1-C6 alkyl;

L$^1$ is a divalent radical of formula -(Alk$^1$)$_m$(Q)$_n$(Alk$^2$)$_p$- wherein m, n and p are independently 0 or 1, Q is (i) an optionally substituted divalent mono- or bicyclic carbocyclic or heterocyclic radical having 5-13 ring members, or (ii), in the case where both m and p are 0, a divalent radical of formula —X$^2$-Q$^1$ or Q$^1$-X$^2$— wherein X$^2$ is —O—, S— or NR$^A$— wherein R$^A$ is hydrogen or optionally substituted C$_1$-C$_3$ alkyl, and Q$^1$ is an optionally substituted divalent mono- or bicyclic carbocyclic or heterocyclic radical having 5-13 ring members, Alk$^1$ and Alk$^2$ independently represent optionally substituted divalent C$_3$-C$_7$ cycloalkyl radicals, or optionally substituted straight or branched, C$_1$-C$_6$ alkylene, C$_2$-C$_6$ alkenylene, or C$_2$-C$_6$ alkynylene radicals which may optionally contain or terminate in an ether (—O—), thioether (—S—) or amino (—NR$^A$—) link wherein R$^A$ is hydrogen or optionally substituted C$_1$-C$_3$ alkyl; and X$^1$ represents a bond; —C(=O); or —S(=O)$_2$—; —NR$_4$C(=O)—, —C(=O)NR$_4$—, —NR$_4$C(=O) NR$_5$—, —NR$_4$S(=O)$_2$—, or —S(=O)$_2$NR$_4$— wherein R$_4$ and R$_5$ are independently hydrogen or optionally substituted C$_1$-C$_6$ alkyl;

R$_1$ is a carboxylic acid group (—COOH), or an ester group which is hydrolysable by one or more intracellular esterase enzymes to a carboxylic acid group; and R$_2$ and R$_3$ are selected from the side chains of a natural or non-natural alpha-amino acid, provided that neither R$_2$ or R$_3$ is hydrogen.

2. A compound as claimed in claim 1 wherein D is optionally substituted phenyl, or optionally substituted pyridynyl.

3. A compound as claimed in claim 1 wherein R$_6$, is hydrogen or methyl.

4. A compound as claimed in claim 1 wherein P is hydrogen and U is a radical of formula (IA) as defined in claim 1.

5. A compound as claimed in claim 1 wherein A is optionally substituted 1,4 phenylene or selected from those of formulae A-X, optionally substituted:

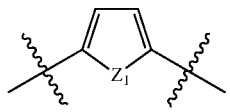

A

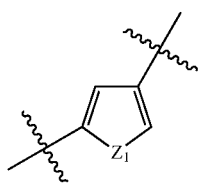

B

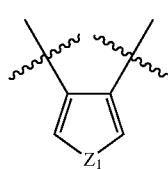

C

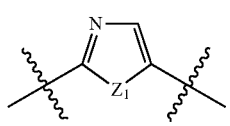

D

-continued

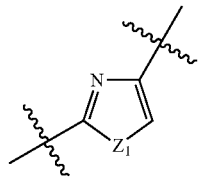

E

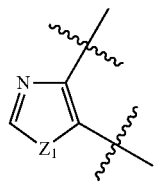

F

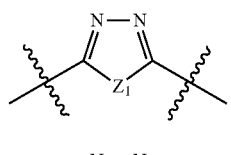

G

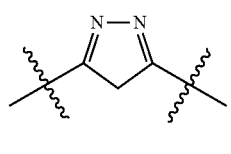

H

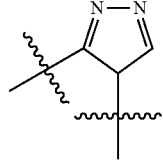

I

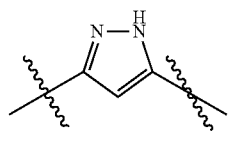

K

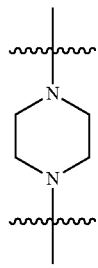

L

M

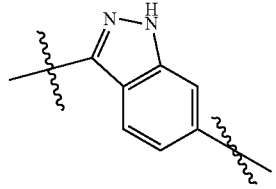

N

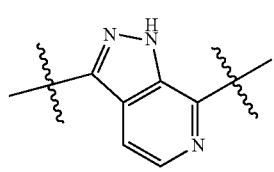

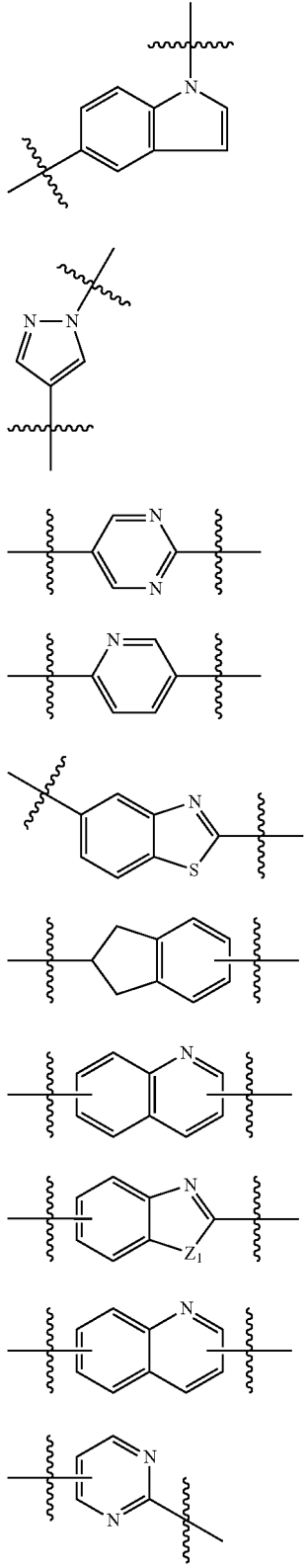

wherein $Z_1$ is NH, S or O.

6. A compound as claimed in claim 1 which has formula (II):

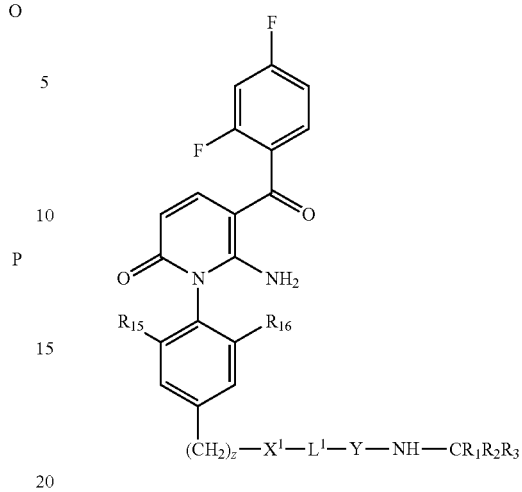

wherein $R_{15}$ and $R_{16}$ are independently hydrogen or fluoro, and wherein z, $X^1$, $L^1$, Y, $R^1$, $R^2$ and $R^3$ are as defined in claim 1.

7. A compound as claimed in claim 1 wherein the radical —Y-$L^1$-$X^1$—[$CH_2$]$_z$—, is —$CH_2$—, —$CH_2CH_2$—, —$CH_2CH_2CH_2$—, —$CH_2CH_2CH_2CH_2$—, —$CH_2O$—, —$CH_2CH_2O$—, —$CH_2CH_2CH_2O$—, —$CH_2CH_2CH_2CH_2O$—, —C(=O)—$CH_2$—, —C(=O)—$CH_2O$—, —C(=O)—NH—$CH_2$—, or —C(=O)—NH—$CH_2O$—.

8. A compound as claimed in claim 1 wherein $R_1$ is an ester group of formula —(C=O)O$R_{14}$ wherein $R_{14}$ is $R_8R_9R_{10}C$— wherein (i) $R_8$ is hydrogen or optionally substituted ($C_1$-$C_3$)alkyl-($Z^1$)$_a$—[($C_1$-$C_3$)alkyl]$_b$- or($C_2$-$C_3$)alkenyl-($Z^1$)$_a$—[($C_1$-$C_3$)alkyl]$_b$- wherein a and b are independently 0 or 1 and $Z^1$ is —O—, —S—, or —N$R_{11}$— wherein $R_{11}$ is hydrogen or ($C_1$-$C_3$)alkyl; and $R_9$ and $R_{10}$ are independently hydrogen or ($C_1$-$C_3$)alkyl-;

(ii) $R_8$ is hydrogen or optionally substituted $R_{12}R_{13}$N—($C_1$-$C_3$)alkyl- wherein $R_{12}$ is hydrogen or —($C_1$-$C_3$)alkyl and $R_{13}$ is hydrogen or —($C_1$-$C_3$)alkyl; or $R_{12}$ and $R_{13}$ together with the nitrogen to which they are attached form an optionally substituted monocyclic heterocyclic ring of 5- or 6-ring atoms or bicyclic heterocyclic ring system of 8 to 10 ring atoms, and $R_9$ and $R_{10}$ are independently hydrogen or ($C_1$-$C_3$)alkyl-; or (iii) $R_8$ and $R_9$ taken together with the carbon to which they are attached form an optionally substituted monocyclic carbocyclic ring of from 3 to 7 ring atoms or bicyclic carbocyclic ring system of 8 to 10 ring atoms, or bridged monocyclic carbocyclic ring system of 7 to 10 ring atoms, and $R_{10}$ is hydrogen;

and wherein in cases (i), (ii) and (iii) above, the term "alkyl" includes fluoroalkyl.

9. A compound as claimed in claim 8 wherein $R_{14}$ is methyl, ethyl, n- or iso-propyl, n-, sec- or tert-butyl, cyclohexyl, allyl, bicyclo[2.2.1]hept-2-yl, 2,3-dihydro-1H-inden-2-yl, phenyl, benzyl, 2-, 3- or 4-pyridylmethyl, N-methylpiperidin-4-yl, or methoxyethyl.

10. A compound as claimed in claim 8 wherein $R_{14}$ is cyclopentyl.

11. A compound as claimed in claim 1 wherein $R_2$ and $R_3$ are selected from phenyl and groups of formula —C$R_aR_bR_c$ in which:

each of $R_a$, $R_b$ and $R_c$ is independently hydrogen, $(C_1-C_6)$alkyl, $(C_2-C_6)$alkenyl, $(C_2-C_6)$alkynyl, phenyl$(C_1-C_6)$alkyl, $(C_3-C_8)$cycloalkyl; or $R_c$ is hydrogen and $R_a$ and $R_b$ are independently phenyl or heteroaryl; or $R_c$ is hydrogen, $(C_1-C_6)$alkyl, $(C_2-C_6)$alkenyl, $(C_2-C_6)$alkynyl, phenyl$(C_1-C_6)$alkyl, $(C_3-C_8)$cycloalkyl, and $R_a$ and $R_b$ together with the carbon atom to which they are attached form a 3 to 8 membered cycloalkyl or a 5- to 6-membered heterocyclic ring; or $R_a$, $R_b$ and $R_c$ together with the carbon atom to which they are attached form a tricyclic ring; or Ra and Rb are each independently $(C_1-C_6)$alkyl, $(C_2-C_6)$alkenyl, $(C_2-C_6)$alkynyl, phenyl$(C_1-C_6)$alkyl, or a group as defined for Rc below other than hydrogen, or Ra and Rb together with the carbon atom to which they are attached form a cycloalkyl or heterocyclic ring, and Rc is hydrogen, —OH, —SH, halogen, —CN, —CO$_2$H, $(C_1-C_4)$perfluoroalkyl, —CH$_2$OH, —O$(C_1-C_6)$alkyl, —O$(C_2-C_6)$alkenyl, —S$(C_1-C_6)$alkyl, —SO$(C_1-C_6)$alkyl, —SO$_2(C_1-C_6)$alkyl, —S$(C_2-C_6)$alkenyl, —SO$(C_2-C_6)$alkenyl, —SO$_2(C_2-C_6)$alkenyl or a group -Q-W wherein Q represents a bond or —O—, —S—, —SO— or —SO$_2$— and W represents a phenyl, phenylalkyl, $(C_3-C_8)$cycloalkyl, $(C_3-C_8)$cycloalkylalkyl, $(C_4-C_8)$cycloalkenyl, (C4-C8)cycloalkenylalkyl, heteroaryl or heteroarylalkyl group, which group W may optionally be substituted by one or more substituents independently selected from, hydroxyl, halogen, —CN, —CONH$_2$, —CONH$(C_1-C_6)$alkyl, —CONH$(C_1-C_6$alkyl$)_2$, —CHO, CH$_2$OH, $(C_1-C_4)$perfluoroalkyl, —O$(C_1-C_6)$alkyl, —S$(C_1-C_6)$alkyl, —SO$(C_1-C_6)$alkyl, SO$_2(C_1-C_6)$alkyl, —NO$_2$, —NH$_2$, —NH$(C_1-C_6)$alkyl, —N$((C_1-C_6)$alkyl$)_2$, —NHCO$(C_1-C_6)$alkyl, $(C_1-C_6)$ alkyl, $(C_2-C_6)$alkenyl, $(C_2-C_6)$alkynyl, $(C_3-C_8)$cycloalkyl, $(C_4-C_8)$cycloalkenyl, phenyl or benzyl.

12. A compound as claimed in claim 1 wherein $R_2$ and $R_3$ taken together with the carbon to which they are attached form a 3-6 membered saturated spiro cycloalkyl or spiro heterocyclyl ring; or wherein at least one of $R_2$ and $R_3$ is a $C_1-C_6$ alkyl substituent.

13. A compound as claimed in claim 1 wherein at least one of $R_2$ and $R_3$ is a $C_1-C_6$ alkyl substituent, and the other is selected from the group consisting of methyl, ethyl, n- and iso-propyl, n-, sec- and tert-butyl, phenyl, benzyl, thienyl, cyclohexyl and cyclohexylmethyl.

14. A compound as claimed in claim 1 wherein one of $R_2$ and $R_3$ is methyl and the other is methyl, ethyl, or n- or iso-propyl; or $R_2$ and $R_3$ taken together with the carbon to which they are attached form a cyclopropyl, cyclobutyl, cyclopentyl or cyclohexyl ring.

15. A compound as claimed in claim 1 selected from the group consisting of:
Cyclopentyl N-(2-{4-[6-amino-5-(2,4-difluorobenzoyl)-2-oxopyridin-1(2H)-yl]phenyl}ethyl)-2-methylalaninate
Cyclopentyl N-(2-{4-[6-amino-5-(2,4-difluorobenzoyl)-2-oxopyridin-1(2H)-yl]-3,5-difluorophenyl}ethyl)-2-methylalaninate and
Cyclopentyl N-(3-{4-[6-amino-5-(2,4-difluorobenzoyl)-2-oxopyridin-1(2H)-yl]-3,5-difluorophenoxy}propyl)-2-methylalaninate.

16. A compound as claimed in claim 1 which is in the form of a pharmaceutically acceptable salt.

17. A pharmaceutical composition comprising a compound as claimed in claim 1, together with a pharmaceutically acceptable carrier.

* * * * *